US011376319B2

(12) United States Patent
Peng et al.

(10) Patent No.: US 11,376,319 B2
(45) Date of Patent: Jul. 5, 2022

(54) RECOMBINANT H7N9 SUBTYPE AVIAN INFLUENZA VIRUS, INACTIVATED MARKED VACCINE AND PREPARATION METHOD THEREOF

(71) Applicant: YANGZHOU UNIVERSITY, Jiangsu (CN)

(72) Inventors: Daxin Peng, Yangzhou (CN); Sujuan Chen, Yangzhou (CN); Zhihao Sun, Yangzhou (CN); Tao Qin, Yangzhou (CN); Qiuxia Wang, Yangzhou (CN); Xiufan Liu, Yangzhou (CN)

(73) Assignee: YANGZHOU UNIVERSITY, Yangzhou (CN)

( * ) Notice: Subject to any disclaimer, the term of this patent is extended or adjusted under 35 U.S.C. 154(b) by 0 days.

(21) Appl. No.: 16/960,222

(22) PCT Filed: May 13, 2019

(86) PCT No.: PCT/CN2019/086620

§ 371 (c)(1),
(2) Date: Jul. 6, 2020

(87) PCT Pub. No.: WO2020/093674

PCT Pub. Date: May 14, 2020

(65) Prior Publication Data

US 2021/0244810 A1 Aug. 12, 2021

(30) Foreign Application Priority Data

Nov. 5, 2018 (CN) ......................... 201811308245.5

(51) Int. Cl.

| | |
|---|---|
| ***A61K 39/145*** | (2006.01) |
| ***C12N 7/00*** | (2006.01) |
| *A61K 39/00* | (2006.01) |

(52) U.S. Cl.
CPC .............. *A61K 39/145* (2013.01); *C12N 7/00* (2013.01); *A61K 2039/5252* (2013.01);
(Continued)

(58) Field of Classification Search
None
See application file for complete search history.

(56) References Cited

U.S. PATENT DOCUMENTS

2018/0303928 A1* 10/2018 Newbury ............. A61K 9/0019
2021/0244810 A1* 8/2021 Peng ........................ C12N 7/00

FOREIGN PATENT DOCUMENTS

CN 107142280 A 9/2017
CN 107449912 A 12/2017
(Continued)

OTHER PUBLICATIONS

Choi et al. (KR 1835989, English translation provided, published Mar. 2018).*
(Continued)

*Primary Examiner* — Shanon A. Foley

(74) *Attorney, Agent, or Firm* — Stetina Brunda Garred & Brucker

(57) ABSTRACT

Provided is a recombinant H7N9 subtype avian influenza virus, a marked vaccine and a preparation method thereof. For the recombinant H7N9 subtype avian influenza virus, a strain JD/17 of H7N9 subtype avian influenza virus is used as parent virus and a peptide sequence in HA protein of the strain JD/17 is replaced with a peptide sequence in HA protein of H3 subtype; the strain JD/17 of H7N9 subtype
(Continued)

avian influenza virus has a preservation number of CCTCC No. V201862. The results of HA titers, EID50, TCID50 show that the rescued virus maintains similar biological characteristics of parent virus, such as high HA titers and EID50, and chickens immunized with the marked inactivated and emulsified vaccine produce a high level of antibody, and this antibody can be distinguished from antibodies produced by chickens naturally infected with H7N9 subtype avian influenza virus.

14 Claims, 4 Drawing Sheets

Specification includes a Sequence Listing.

(52) U.S. Cl.
CPC .................. *A61K 2039/552* (2013.01); *C12N 2760/16121* (2013.01); *C12N 2760/16122* (2013.01); *C12N 2760/16134* (2013.01); *C12N 2760/16162* (2013.01)

(56) References Cited

FOREIGN PATENT DOCUMENTS

| | | |
|---|---|---|
| CN | 107765001 A | 3/2018 |
| CN | 109402070 A | 3/2019 |

OTHER PUBLICATIONS

DesRochers et al. (Vaccine; 2016; 494: 89-99).*
SEQ ID 1 alignment with UniProt db access No. V9SVH8_9INFA Mar. 2014.*
SEQ ID 2 alignment with UniProt db access No. 5IRV2_9INFA Jan. 2014.*
Hou et al. (CN 103520716, English translation provided, published Jan. 2014).*
Derwent abstract of CN 101607084, published Jun. 2008.*
The Derwent abstract of CN 107875383, published Apr. 2018.*
Schmeisser, Falko; Vasudevan Anupama; Verma, Swati; Wang, Wei; Alvarado, Esmeralda; Weiss, Carol; Atukorale, Vajini; Meseda, Clement; Weir, Jerry P.; “Antibodies to Antigenic Site A of Influenza H7 Hemagglutinin Provide Protection Against H7H9 Challenge”; Jan. 28, 2015.

* cited by examiner

```
┌─────────────────────────────────────────┐
│ Isolation and Identification of H7N9    │
│ subtype avian influenza virus           │
└─────────────────────────────────────────┘
                    │
                    ▼
┌─────────────────────────────────────────┐
│ Determination of binding capacity of    │
│ polypeptides and immune antibody        │
│ against different subtypes of avian     │
│ influenza viruses                       │
└─────────────────────────────────────────┘
                    │
                    ▼
┌─────────────────────────────────────────┐
│ Determination of specific epitopes of   │
│ HA2 protein in H7N9 subtype avian       │
│ influenza virus                         │
└─────────────────────────────────────────┘
                    │
                    ▼
┌─────────────────────────────────────────┐
│ Construction of a recombinant H7N9      │
│ subtype avian influenza virus with the  │
│ replaced specific epitopes of HA2       │
│ protein                                 │
└─────────────────────────────────────────┘
                    │
                    ▼
┌─────────────────────────────────────────┐
│ Determination of biological             │
│ characteristics of DIVA vaccine virus   │
└─────────────────────────────────────────┘
                    │
                    ▼
┌─────────────────────────────────────────┐
│ Determination of immune protection      │
│ effects of DIVA vaccine                 │
└─────────────────────────────────────────┘
                    │
                    ▼
┌─────────────────────────────────────────┐
│ Determination of corresponding          │
│ polypeptide antibody after immunization │
│ with DIVA vaccine                       │
└─────────────────────────────────────────┘
```

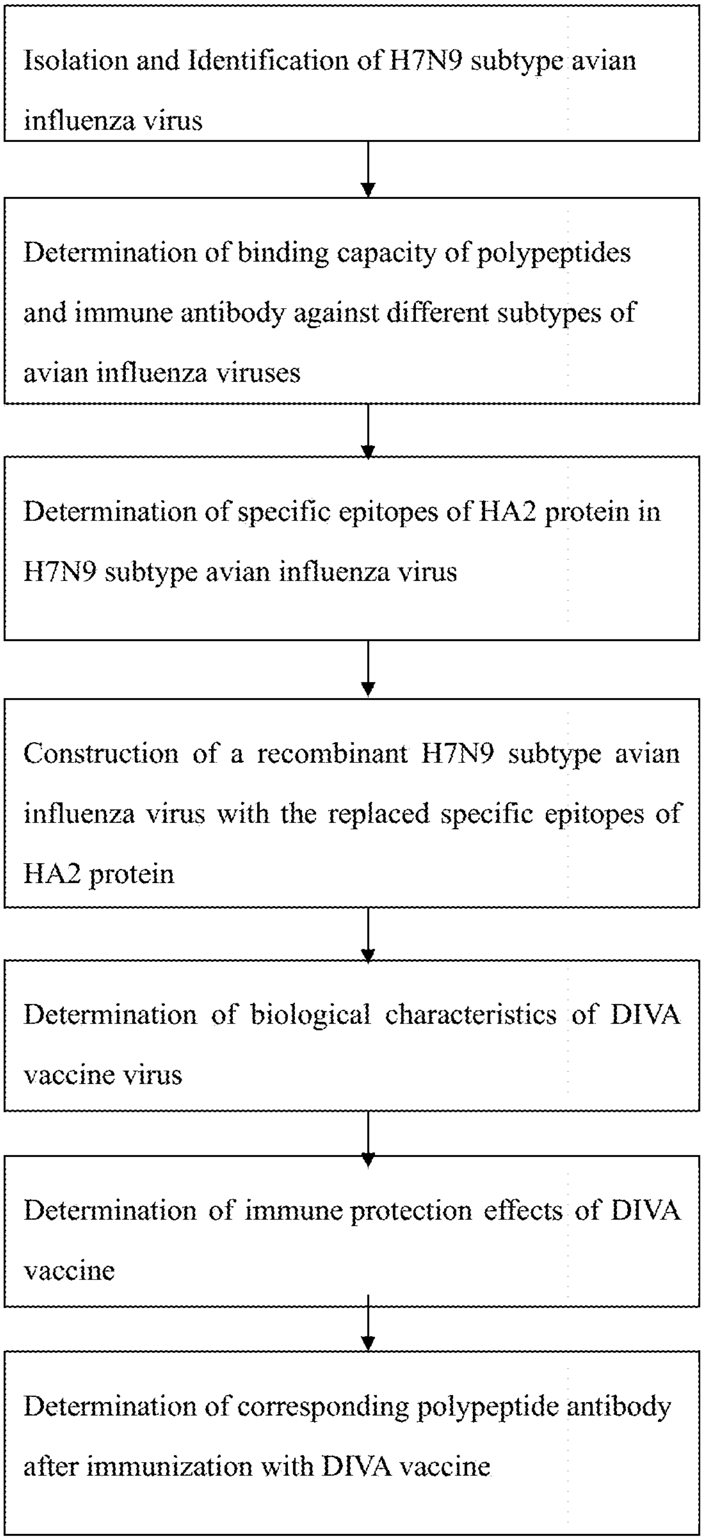

FIG. 1

SEQUENCE LISTING

```
<160> NUMBER OF SEQ ID NOS: 43

<210> SEQ ID NO 1
<211> LENGTH: 20
<212> TYPE: PRT
<213> ORGANISM: Orthomyxoviridae Alphainfluenza virus

<400> SEQUENCE: 1

Ala Asp Ser Glu Met Asn Lys Leu Phe Glu Lys Thr Lys Lys Gln Leu
1               5                   10                  15

Arg Glu Asn Ala
            20

<210> SEQ ID NO 2
<211> LENGTH: 20
<212> TYPE: PRT
<213> ORGANISM: Orthomyxoviridae Alphainfluenza virus

<400> SEQUENCE: 2

Ala Asp Ser Glu Met Asp Lys Leu Tyr Glu Arg Val Lys Arg Gln Leu
1               5                   10                  15

Arg Glu Asn Ala
            20

<210> SEQ ID NO 3
<211> LENGTH: 45
<212> TYPE: DNA
<213> ORGANISM: Artificial Sequence
<220> FEATURE:
<223> OTHER INFORMATION: The nucleotide sequence of KS-H7-1

<400> SEQUENCE: 3
gacctccgaa gttggggggg agcaaaagca ggggatacaa aatga                      45

<210> SEQ ID NO 4
<211> LENGTH: 40
<212> TYPE: DNA
<213> ORGANISM: Artificial Sequence
<220> FEATURE:
<223> OTHER INFORMATION: The nucleotide sequence of JDH7H3-1-R

<400> SEQUENCE: 4
aaaaatttcg ttcagtttca acatttctga atcagccaga                            40

<210> SEQ ID NO 5
<211> LENGTH: 40
<212> TYPE: DNA
<213> ORGANISM: Artificial Sequence
<220> FEATURE:
<223> OTHER INFORMATION: The nucleotide sequence of JDH7H3-2-F

<400> SEQUENCE: 5
tgaacgaaat ttttaaaatg cagctgagag agaatgctga                            40

<210> SEQ ID NO 6
<211> LENGTH: 48
<212> TYPE: DNA
<213> ORGANISM: Artificial Sequence
<220> FEATURE:
<223> OTHER INFORMATION: The nucleotide sequence of KS-H7-2

<400> SEQUENCE: 6
gcattttggg ccgccgggtt attagtagaa acaagggtgt tttttcca                   48
```

-continued

<210> SEQ ID NO 7
<211> LENGTH: 28
<212> TYPE: DNA
<213> ORGANISM: Artificial Sequence
<220> FEATURE:
<223> OTHER INFORMATION: Ba -PB2-F

<400> SEQUENCE: 7
tattggtctc agggagcgaa agcaggtc 28

<210> SEQ ID NO 8
<211> LENGTH: 34
<212> TYPE: DNA
<213> ORGANISM: Artificial Sequence
<220> FEATURE:
<223> OTHER INFORMATION: Ba -PB2-R

<400> SEQUENCE: 8
atatggtctc gtattagtag aaacaaggtc gttt 34

<210> SEQ ID NO 9
<211> LENGTH: 28
<212> TYPE: DNA
<213> ORGANISM: Artificial Sequence
<220> FEATURE:
<223> OTHER INFORMATION: Bm-PB1-F

<400> SEQUENCE: 9
tattcgtctc agggagcgaa agcaggca 28

<210> SEQ ID NO 10
<211> LENGTH: 33
<212> TYPE: DNA
<213> ORGANISM: Artificial Sequence
<220> FEATURE:
<223> OTHER INFORMATION: Bm-PB1-R

<400> SEQUENCE: 10
atatcgtctc gtattagtag aaacaaggca ttt 33

<210> SEQ ID NO 11
<211> LENGTH: 29
<212> TYPE: DNA
<213> ORGANISM: Artificial Sequence
<220> FEATURE:
<223> OTHER INFORMATION: Bm-PA-F

<400> SEQUENCE: 11
tattcgtctc agggagcgaa agcaggtac 29

<210> SEQ ID NO 12
<211> LENGTH: 33
<212> TYPE: DNA
<213> ORGANISM: Artificial Sequence
<220> FEATURE:
<223> OTHER INFORMATION: Bm-PA-R

<400> SEQUENCE: 12
atatcgtctc gtattagtag aaacaaggta ctt 33

<210> SEQ ID NO 13
<211> LENGTH: 28
<212> TYPE: DNA
<213> ORGANISM: Artificial Sequence
<220> FEATURE:
<223> OTHER INFORMATION: Bm-HA-F

<400> SEQUENCE: 13
tattcgtctc agggagcraa agcagggg 28

<210> SEQ ID NO 14
<211> LENGTH: 35
<212> TYPE: DNA
<213> ORGANISM: Artificial Sequence
<220> FEATURE:
<223> OTHER INFORMATION: Bm-HA-R

<400> SEQUENCE: 14
atatcgtctc gtattagtag aaacaagggt gtttt 35

<210> SEQ ID NO 15
<211> LENGTH: 32
<212> TYPE: DNA
<213> ORGANISM: Artificial Sequence
<220> FEATURE:
<223> OTHER INFORMATION: Bm-NP-F

<400> SEQUENCE: 15
tattcgtctc agggagcaaa agcagggtag at 32

<210> SEQ ID NO 16
<211> LENGTH: 34
<212> TYPE: DNA
<213> ORGANISM: Artificial Sequence
<220> FEATURE:
<223> OTHER INFORMATION: Bm-NP-R

<400> SEQUENCE: 16
atatcgtctc gtattagtag aaacaagggt attt 34

<210> SEQ ID NO 17
<211> LENGTH: 29
<212> TYPE: DNA
<213> ORGANISM: Artificial Sequence
<220> FEATURE:
<223> OTHER INFORMATION: Ba-NA-F

<400> SEQUENCE: 17
tattggtctc agggagcaaa agcaggagt 29

<210> SEQ ID NO 18
<211> LENGTH: 36
<212> TYPE: DNA
<213> ORGANISM: Artificial Sequence
<220> FEATURE:
<223> OTHER INFORMATION: Ba-NA-R

<400> SEQUENCE: 18
atatggtctc gtattagtag aaacaaggag tttttt 36

<210> SEQ ID NO 19
<211> LENGTH: 29
<212> TYPE: DNA
<213> ORGANISM: Artificial Sequence
<220> FEATURE:
<223> OTHER INFORMATION: Bm-M-F

<400> SEQUENCE: 19
tattcgtctc agggagcaaa agcaggtag 29

<210> SEQ ID NO 20
<211> LENGTH: 36

<212> TYPE: DNA
<213> ORGANISM: Artificial Sequence
<220> FEATURE:
<223> OTHER INFORMATION: Bm-M-R

<400> SEQUENCE: 20
atatcgtctc gtattagtag aaacaaggta gttttt 36

<210> SEQ ID NO 21
<211> LENGTH: 31
<212> TYPE: DNA
<213> ORGANISM: Artificial Sequence
<220> FEATURE:
<223> OTHER INFORMATION: Bm-NS-F

<400> SEQUENCE: 21
tattcgtctc agggagcaaa agcagggtga c 31

<210> SEQ ID NO 22
<211> LENGTH: 35
<212> TYPE: DNA
<213> ORGANISM: Artificial Sequence
<220> FEATURE:
<223> OTHER INFORMATION: Bm-NS-R

<400> SEQUENCE: 22
atatcgtctc gtattagtag aaacaagggt gtttt 35

<210> SEQ ID NO 23
<211> LENGTH: 2482
<212> TYPE: DNA
<213> ORGANISM: Artificial Sequence
<220> FEATURE:
<223> OTHER INFORMATION: PB2

<400> SEQUENCE: 23
atgctcccgg ccgccatggc ggccgcggga attcgattgg atcgcccttt attggtctca 60
gggagcgaaa gcaggtcaaa tatattcaat atggagagaa taaaagaact aagagatcta 120
atgtcacagt cccgcacccg cgagatactg acaaaaacca ctgtggacca tatggccata 180
atcaagaaat acacatcagg aagacaagaa aagaaccctg ccctcaaaat gaaatggatg 240
atggcaatga aatatccaat cacagcagac aagagaataa tggagatgat ccctgaacgg 300
aatgaacagg gacaaacgct ttggagcaag gcaaatgatg ctggatcgga cagggtgatg 360
gtgtctcccc tagctgtgac ttggtggaac aggaatggac cgacaacaag tacagtccat 420
tatccaaagg tttacaaaac atactttgag aaggttgaaa ggttaaaaca tggaaccttt 480
ggtcccgtcc atttccgaaa ccaagttaaa atacgccgcc gagtggatat aaacccgggc 540
catgcagatc tcagtgctaa agaagcacaa gatgttatca tggaggttgt tttcccaaat 600
gaagtgggag ctagaatatt gacatcagag tcgcaattga caataacaaa agagaagaag 660
gaagagctcc aggattgtaa gattgctcct ttaatggtgg catacatgct ggaaagagaa 720
ctggtccgca aaaccagatt tctaccggta gcaggcggaa caagcagtgt atacattgag 780
gtattacatt tgactcaagg gacctgttgg gaacagatgt acactcctgg tggagaagtg 840
agaaatgatg atgttgacca gagtttgatc atcgctgcca gaaacattgt taggagagca 900
acagtatcgg cggacccact ggcatcacta ctggagatgt gtcacagcac acaaattggt 960
ggaataagga tggtagacat tcttaggcaa aatcccactg aggaacaagc tgtggatata 1020
tgcaaagcag caatgggctt gaggatcagt tcatctttta gctttggagg cttcactttc 1080

-continued

```
aaaaggacaa gtgggtcatc cgtaaagaaa gaagaagaaa tgcttacagg caacctccaa   1140
acattgaaaa taaaagtgca tgaggggtat gaagaattca caatggttgg gcggagagca   1200
acagctatcc tgaggaaagc aactaggagg ctgattcaat tgatagtaag tggaagagat   1260
gagcaatcaa tcgctgaagc gatcattgta gcaatggtgt tctcacagga ggattgcatg   1320
ataaaggcag tccgaggcga tctgaatttc gtaaacagag caaaccaaag attgaacccc   1380
atgcatcagc tattgaggca cttccaaaaa gatgcaaaag tgctgtttca gaactgggga   1440
attgaaccta ttgacaatgt catggggatg atcgggatac tacctgacat gactccaagc   1500
acagagatgt cactgagagg ggtgagagtt agtaagatgg gagtggatga atactccagc   1560
actgagagag tagttgtgag tattgaccgt ttcttgaggg tccgagatca gcgagggaat   1620
gtactcttat cccctgaaga ggttagtgaa acacagggaa cggagaagtt aacaataaca   1680
tattcatcct caatgatgtg ggaaatcaac ggccctgagt cagtgcttgt taatacttat   1740
cagtggatca tcaggaattg ggaggctgta aagattcaat ggtctcaaga tcccacaatg   1800
ctatacaata agatggaatt tgaaccattc caatccttag tgcccaaggc cgccagaggc   1860
caatacagtg ggtttgtgag aacacttttc caacaaatgc gtgatgttct ggggacgttt   1920
gatactgttc aaataataaa gctgctacca tttgcagcag ccccaccgga acaaagcaga   1980
atgcagtttt cttctctaac tgtgaatgtg agaggttcag gaatgagaat actcgtgagg   2040
ggcaactccc ccgtgttcaa ctacaacaag gcaactaaaa ggcttacagt cctcgggaag   2100
gacgcaggtg cattaacaga agatccagac gagggaacag ccggggttga atctgcggta   2160
ctgaggggat tcctaattct aggcaaggaa gacaaaagat atggaccagc attgagcatc   2220
aatgaactga gcaatcttgc aaaaggggag aaggctaatg tgctaatagg gcaaggggac   2280
gtggtgttgg taatgaaacg gaaacgggac tccagcatac ttactgacag ccagacagcg   2340
accaaaagaa ttcggatggc catcaattag tgtcgaattg tttaaaaacg accttgtttc   2400
tactaatacg agaccatata agggcgatcc caatcactag tgaattcgcg gccgcctgca   2460
ggtcgaccat atgggagagc tc                                             2482
```

<210> SEQ ID NO 24
<211> LENGTH: 2398
<212> TYPE: DNA
<213> ORGANISM: Artificial Sequence
<220> FEATURE:
<223> OTHER INFORMATION: PB1

<400> SEQUENCE: 24

```
atggatgtca atccgacttt acttttcttg aaagtaccag tgcaaaatgc tataagtacc     60
acattccctt atactggaga ccctccatac agccatggaa cagggacagg atacaccatg    120
gacacagtca accgaacaca ccaatattca gaaaagggga agtggacaac aaacacagag    180
actggagcac cccaactcaa cccgattgat ggaccactac ctgaggataa tgagcccagt    240
gggtatgcac aaacagattg tgtattggaa gcaatggctt tccttgaaga atcccaccca    300
gggatctttg aaaactcgtg tcttgaaacg atggaaattg ttcaacaaac aagagtggat    360
aaactgaccc aaggtcgcca gacttatgac tggacattga atagaaacca accggctgca    420
actgctttgg ccaacactat agaaatcttc agatcgaacg gtctgacagc aaatgaatcg    480
ggacggctaa tagatttcct caaggatgtg atggaatcaa tggataagga agaaatggag    540
ataacaacac atttccagag aaagagaaga gtaagggaca acatgaccaa gaaaatggta    600
acacaaagaa caatagggaa gaaaaaacaa aggctgaaca aaaagagcta cctgataaga    660
```

gcactgacac tgaacacaat gacaaaagat gcagaaagag gcaaattgaa gaggcgagca 720
attgcaacac ccggaatgca aatcagagga ttcgtgtact ttgttgaaac actagcgagg 780
agtatctgtg agaaacttga gcaatctgga ctcccagtcg gagggaatga gaagaaagct 840
aaattggcaa acgtcgtgag gaagatgatg accaactcac aggatactga actctccttt 900
acaattactg ggacaatac caaatggaat gagaatcaga atcctaggat gtttctggca 960
atgataacgt acatcacaag gaaccagcca gaatggtttc gaaatgtctt aagcattgcc 1020
cctataatgt tctcaaacaa gatggcgaga ttaggaaaag gatacatgtt cgaaagtaag 1080
agcatgaagt tacgaacaca aataccagca gaaatgcttg caaacattga tcttaaatac 1140
ttcaatgaat taacgaaaaa gaaaattgag aaaataagac ctctattaat agatggtgca 1200
gcctcattga gccctggaat gatgatgggc atgttcaaca tgctgagtac agtcctagga 1260
gtctcaatcc tgaatcttgg acagaaaagg tacaccaaaa ccacatattg gtgggacgga 1320
ctccaatcct ctgatgattt cgctctcatc gtaaatgcac cgaatcatga gggaatacaa 1380
gcaggagtgg ataggtttta taggacttgt aaactagttg gaatcaatat gagcaagaag 1440
aagtcttaca taaatcggac agggacattt gaattcacga gctttttcta ccgctatgga 1500
tttgtagcca atttcagtat ggagctgccc agttttggag tgtctggaat taatgaatcg 1560
gccgacatga gcattggtgt tacagtgata aagaacaata tgataaacaa cgaccttggg 1620
ccagcaacag ctcagatggc tcttcagcta ttcatcaagg actacagata cacataccga 1680
tgccacagag ggatacgca aatccaaacg aggagatcat tcgagctgaa gaagctatgg 1740
gagcaaaccc gttcaaaagc aggactgttg gtttcagatg gaggaccaaa cctatacaat 1800
atccgaaatc tccatattcc tgaggtctgc ttgaaatggg aattgatgga tgaagattac 1860
caaggcagac tgtgcaatcc tctgaatcca ttcgtcagcc ataaggaaat tgaatctgtc 1920
aacaatgcta tagtaatgcc agctcatggt ccggccaaga gtatggaata tgatgccgtt 1980
gcaactacac attcatggat ccctaaaagg aatcgttcca ttctcaatac gagtcaaagg 2040
ggaattcttg aggatgaaca gatgtaccaa aagtgctgca atctattcga gaaattcttc 2100
cccagcagtt catatcggag gccagttgga atttccagca tggtggaggc catggtgtct 2160
agggcccgaa ttgacgcacg aattgatttc gagtctggaa ggatcaagaa agaagagttt 2220
gctgagatca tgaagatctg ttccaccatt gaagagctca gacggcaaaa atagtgaatt 2280
tagcttgtcc ttcgtgaaaa aatgccttgt ttctactaat acgagacgat ataagggcga 2340
tcccaatcac tagtgaattc gcggccgcct gcaggtcgac catatgggag agctccca 2398

<210> SEQ ID NO 25
<211> LENGTH: 2287
<212> TYPE: DNA
<213> ORGANISM: Artificial Sequence
<220> FEATURE:
<223> OTHER INFORMATION: PA

<400> SEQUENCE: 25
atggaagact ttgtgcgaca atgcttcaac ccaatgattg tcgagcttgc ggaaaaggca 60
atgaaagaat atggggaaga cccgaaaatc gaaacgaaca aatttgctgc aatatgcaca 120
cacttggagg tctgtttcat gtattcggat tttcacttta ttgatgaacg gagtgaatca 180
ataattgtag aatctggaga tccgaatgca ttattgaaac accgatttga aataattgaa 240
ggaagagacc gaacgatggc ctggactgtg gtgaatagta tttgcaacac cacaggagtc 300

-continued

```
gagaaaccta aatttctccc agatttgtat gactacaaag agaaccgatt cattgaaatt    360
ggagtgacac gaagggaagt tcatacatac tatctggaga aagccaacaa gataaaatcc    420
gagaagacac acattcacat attctcattc acaggggagg aaatggccac caaagcggac    480
tacacccttg atgaagagag cagggcgaga attaaaacca ggctgttcac cataagacag    540
gaaatggcca gtaggggtct atgggattcc tttcgccaat ccgagagagg cgaagagaca    600
attgaagaaa aatttgaaat cactggaacc atgcgcagac ttgccgacca aagtctccca    660
ccgaacttct ccagccttga aaactttaga gcctatgtgg atggattcga accgaacggc    720
tgcattgagg gcaagctttc tcaaatgtca aaagaagtga atgctgaaat tgagccattt    780
ttgaagacaa cgccacgccc tctcagatta cctgatgggc ctccttgctc tcagcggtcg    840
aagttcttgc tgatggatgc ccttaaacta agcatcgaag atccgagtca tgagggggag    900
gggataccac tatacgatgc aatcaaatgc atgaagacat ttttcggctg gaaggagccc    960
aacatcgtga aaccacatga aaaaggtata aaccccaatt acctcctggc ttggaagcaa   1020
gtgctggcag aactccaaga tattgaaaat gaggagaaaa tcccaaaaac aaagaacatg   1080
aagaaaacaa gccaattaaa gtgggcactc ggtgagaaca tggcaccaga gaaagtagac   1140
tttgaggact gcaaagatat cagcgatcta agacagtatg acagtgatga accagagtct   1200
agatcactag caagctggat tcagagtgaa ttcaacaaag catgtgaatt aacagattcg   1260
agttggattg aacttgatga aataggagag gacgttgctc caattgagca cattgcaagt   1320
atgagaagga actattttac agcggaagta tcccattgca gagccactga atacataatg   1380
aagggagtgt acataaacac agccctgttg aatgcatcct gtgcagccat ggatgacttt   1440
caactaattc caatgataag caaatgcaga accaaagaag gaagacggaa aactaatctg   1500
tatggattca ttataaaggg aagatcccac ttgaggaatg ataccgatgt ggtaaatttt   1560
gtgagtatgg aattctctct tactgatccg agactggagc cacacaagtg ggaaaagtac   1620
tgtgttctcg agataggaga catgctcctc cggactgcag taggtcaagt ttcaaggccc   1680
atgttcctgt atgtgagaac caacgggacc tccaagatca aaatgaaatg ggcatggaa    1740
atgaggcgat gccttcttca atcccttcaa caaattgaaa gcatgattga agccgagtct   1800
tctgtcaagg agaaggacat gaccaaagaa ttctttgaaa acaaatcaga aacatggccg   1860
attggagagt cccccaaggg agtggaggaa ggctccatcg gaaaggtgtg cagaaccttg   1920
ctggcgaagt ctgtgttcaa cagtttgtat gcatcttcac aactcgaggg gttttcagct   1980
gaatcaagaa aattgcttct cattgctcag gcacttaggg acaacctgga acctgggacc   2040
ttcgatcttg gagggctata tgaagcaatt gaggagtgcc tgattaacga tccctgggtt   2100
ttgctcaatg cgtcttggtt caactccttc ctcgcacatg cactgaaata gttgtggcaa   2160
tgctactatt tgctatccat actgtccaaa aaagtacctt gtttctacta atacgagacg   2220
atataagggc gatccaatcg aattcccgcg gccgccatgg cggccgggag catgcgacgt   2280
cgggccc                                                             2287
```

<210> SEQ ID NO 26
<211> LENGTH: 1683
<212> TYPE: DNA
<213> ORGANISM: Artificial Sequence
<220> FEATURE:
<223> OTHER INFORMATION: HA

<400> SEQUENCE: 26

```
atgaacactc aaatcctggt attcgctctg attgcgatca ttccaacaaa tgcagacaaa     60
```

```
atctgcctcg gacatcatgc cgtgtcaaac ggaaccaaag taaacacatt aactgaaaga    120

ggagtggaag tcgtcaatgc aactgaaaca gtagaacgaa caaacatccc caggatctgc    180

tcaaaaggga aaaagacaat tgacctcggt caatgtggac tactggggac aatcactgga    240

ccacctcaat gtgaccaatt cctagaattt tcagccgatt taattattga gaggcgagaa    300

ggaagtgatg tctgttatcc tggaaaattc gtgaatgaag aagctctgag gcaaattctc    360

agagaatcag gcggaattga caaggaagca atgggattca catacagtgg aataagaact    420

aatggagcaa ccagtgcatg taggagatca ggatcttcat tctatgcaga aatgaaatgg    480

ctcctgtcaa acacagataa tgctacattc ccgcagatga ctaagtcata taaaaataca    540

agaaaaagcc cagctctaat agtatggggg atccatcatt ctgtatcaac tgcagagcaa    600

accaaactat atgggagtgg aaacaaactg gtgacagttg ggagttctaa ttatcaacaa    660

tcttttgtac cgagtccagg agcgagacca caagttaatg gtcaatctgg aagaattgac    720

tttcattggc taatgctaaa tcccaatgat acagtcactt tcagtttcaa tggggctttc    780

atagctccag accgtgcaag cttcctgaga ggaaaatcta tgggaatcca gagtggagta    840

caggttgatg ccaattgtga aggggactgc tatcatagtg gaggaacaat aacaagtaac    900

ttgccatttc agaacataga tagcagggca gttggaaaat gtccgagata tgttaagcaa    960

aagagtctgc tgctagcaac agggatgaag aatgttcctg agattccaaa gggaagaggc   1020

ctatttggtg ctatagcggg tttcattgaa aatggatggg aaggcctaat tgatggttgg   1080

tatggtttca gacaccagaa tgcacaggga gagggaactg ctgcagatta caaaagcact   1140

caatcggcaa ttgatcaaat aacaggaaaa ttaaaccggc ttatagaaaa aaccaaccaa   1200

caatttgagt tgatagacaa tgaattcaat gaggtagaga aacaaatcgg taatgtgata   1260

aattggacca gagattctat aacagaagtg tggtcataca atgctgaact cttggtagca   1320

atggagaacc agcatacaat tgatctggct gattcagaaa tggacaaact gtacgaacga   1380

gtgaaaagac agctgagaga gaatgctgaa gaagatggca ctggttgctt tgaaatattt   1440

cacaagtgtg atgatgactg tatggccagt attagaaata acacctatga tcacagcaag   1500

tacagggaag aggcaatgca aaatagaata cagattgacc cagtcaaact aagcagcggc   1560

tacaaagatg tgatactttg gtttagcttc ggggcatcat gtttcatact tctagccatt   1620

gtaatgggcc ttgtcttcat atgtgtaaag aatggaaaca tgcggtgcac tatttgtata   1680

taa                                                                 1683
```

<210> SEQ ID NO 27
<211> LENGTH: 1497
<212> TYPE: DNA
<213> ORGANISM: Artificial Sequence
<220> FEATURE:
<223> OTHER INFORMATION: NP

<400> SEQUENCE: 27

```
atggcgtctc aaggcaccaa acgatcctat gaacagatgg aaactggtgg ggaacgccag     60

aatgctactg agatcagggc atctgttgga agaatggtta gcggcattgg gagattctac    120

atacagatgt gtacagaact caaactcagt gacaatgaag ggaggctgat tcagaacagt    180

ataacaatag agagaatggt actctctgca tttgatgaaa gaaggaacag atacctggaa    240

gagcacccca gtgcaggaaa ggaccctaag aaaactggag gtccaattta caggagaaga    300

gacggaaaat gggtgagaga gctgatcctg tatgacaaag aggaaatcag gagaatttgg    360
```

-continued

```
cgacaagcga acaatggaga ggatgcaact gctggtctta cccatctgat gatatggcat    420
tccaacctga atgatgctac ctatcagaga acgagagctc tcgtgcgtac tggaatggat    480
ccccggatgt gctctctgat gcaaggatca actctcccga ggagatctgg agctgcaggt    540
gcagcagtga aggggatagg gacaatggtg atggaactga ttcggatgat aaaacgaggg    600
atcaacgacc ggaatttctg gagaggcgaa aatggaagaa ggacaagaat tgcatatgag    660
agaatgtgca acatcctcaa agggaaattc caaacagcag cacaaagggc aatgatggat    720
caagtgcgag agagcagaaa tcctgggaat gctgaaatag aagatctcat tttctggca    780
aggtctgcac tcatcctgag aggatcagtg gcccataaat cctgcttgcc tgcttgtgtg    840
tacggacttg cagtggctag tggatatgac tttgagagag aagggtactc cttggttgga    900
atagatcctt tccgtctgct tcaaaacagc caggtcttta gtctcattag accaaatgag    960
aacccagcac ataagagcca actagtgtgg atggcatgcc actctgcagc gtttgaggac   1020
cttagggtct caagtttcat tagagggaca agaatggtcc caagaggaca gctatccact   1080
agaggggttc aaattgcttc aaatgagaac atggaagcaa tggactccaa tactcttgaa   1140
ctgagaagta gatattgggc tataagaacc agaagcggag ggaacaccaa ccaacagagg   1200
gcatctgcag gacaggtcag cgttcaaccc actttctcag tacagagaaa ccttcctttc   1260
gaaagagcaa ccattatggc agcatttaca ggaaatactg agggtagaac gtctgacatg   1320
aggactgaga tcataagaat gatggaaagt gccagaccag aagatgtgtc attccagggg   1380
cggggagtct tcgagctctc ggacgaaaag gcaacgaacc cgatcgtgcc ttcctttgac   1440
atgaataatg aaggatctta tttcttcgga gacaatgcag aggagtatga caattga      1497
```

<210> SEQ ID NO 28
<211> LENGTH: 1663
<212> TYPE: DNA
<213> ORGANISM: Artificial Sequence
<220> FEATURE:
<223> OTHER INFORMATION: NA

<400> SEQUENCE: 28

```
atgaatccaa atcagaagat tctatgcact tcagccactg ctatcataat aggcgcaatc     60
gcagtactca ttggaatagc aaacctagga ttgaacatag gactgcatct aaaaccgggc    120
tgcaattgct cacactcaca acctgaaaca accaacacaa gccaaacaat aataaacaac    180
tattataatg aaacaaacat caccaacatc caaatggaag agagaacaag caggaatttc    240
aataacttaa ctaaagggct ctgtactata aattcatggc acatatatgg gaaagacaat    300
gcagtaagaa ttggagagag ctcggatgtt ttagtcacaa gagaacccta tgtttcatgc    360
gacccagatg aatgcaggtt ctatgctctc agccaaggaa caacaatcag agggaaacac    420
tcaaacggaa caatacacga taggtcccag tatcgcgccc tgataagctg gccactatca    480
tcaccgccca cagtgtacaa cagcagggtg gaatgcattg ggtggtcaag cactagttgc    540
catgatggca aatccaggat gtcaatatgt atatcaggac caaacaacaa tgcatctgca    600
gtagtgtggt acaacagaag gcctgttgca gaaattaaca catgggcccg aaacatacta    660
agaacacagg aatctgaatg tgtatgccac aatggcatat gcccaatagt gttcaccgat    720
gggtctgcca ctggacctgc agacacaaga atatactatt ttaaagaggg gaaaatattg    780
aaatgggagt ctctgactgg aactgctaag catattgaag aatgctcatg ttacggggaa    840
cgaacaggaa ttacctgcac atgcagggac aattggcagg gctcaaatag accagtgatt    900
cagatagacc cagtagcaat gacacacact agtcaatata tatgcagtcc tgttcttaca    960
```

```
gacactcccc gaccgaatga cccaaatata ggtaagtgta atgaccctta tccaggtaat   1020

aacaacaatg gagtcaaggg gttctcatac ctggatgggg ctaacacttg gctagggagg   1080

acaataagca cagcctcgag gtctggatac gagatgttaa aagtgccaaa tgcattgaca   1140

gatgatagat caaagcccat tcaaggtcag acaattgtat taaacgctga ctggagtggt   1200

tacagtggat ctttcatgga ctattgggct gaaggggact gctatcgagc gtgtttttat   1260

gtggagttga tacgaggaag acccaaggag gataaagtgt ggtggaccag caatagtata   1320

gtatcgatgt gttccagtac agaattcctg ggacaatgga actggcctga tggggctaga   1380

atagagtact tcctctaaga tgaagaaaaa gacccttgtt tctactaata acccggcggc   1440

ccaaaatgcc gactcggagc gaaagatata cctcccccgg ggccgggagg tcgcgtcacc   1500

gaccacgccg ccggcccagg cgacgcgcga cacggacacc tgtccccaaa aacgccacca   1560

tcgcagccac acacggagcg cccggggccc tctggtcaac cccaggacac acgcgggagc   1620

agcgccgggc cggggacgcc ctcccggcgg tcacctaaat gca                      1663
```

```
<210> SEQ ID NO 29
<211> LENGTH: 1224
<212> TYPE: DNA
<213> ORGANISM: Artificial Sequence
<220> FEATURE:
<223> OTHER INFORMATION: M

<400> SEQUENCE: 29

atgtttaaag atgagtcttc taaccgaggt cgaaacgtac gttctctcta tcattccatc     60

aggccccctc aaagccgaga tcgcgcagag acttgaggat gtttttgcag ggaagaacgc    120

agatctcgag gctctcatgg agtggataaa gacaagacca atcctgtcac ctctgactaa    180

ggggatttta gggtttgtgt tcacgctcac cgtgcccagt gagcgaggac tgcagcgtag    240

acggtttgtc caaaccgccc taaatgggaa tggagaccca aacaacatgg acaaggcagt    300

taaattatac aagaaactga agagggaaat gacatttcat ggagcaaagg aagttgcact    360

cagttactca actggtgcgc ttgccagctg catgggtctc atatacaaca ggatggggac    420

agtaactgca gaaggggctc ttggattggt atgtgccact tgtgagcaga ttgctgatgc    480

acaacatcgg tcccacaggc agatggcaac tattaccaac ccactaatta ggcatgagaa    540

tagaatggta ctagccagta ctacggctaa ggctatggag cagatggctg ggtcaagtga    600

acaggcagcg gaagccatgg aagtcgcaag ccaggctagg caaatggtgc aggctatgag    660

gacagtcggg actcacccta actccagtac aggtctaaag gatgatctta ttgaaaattt    720

gcaggcttac cagaaccgga tgggagtgca actgcagcgg ttcaagtgac cctctcgttg    780

ttgcagctaa cattgttggg atattgcact tgatattgtg gattcttgat cgtctttttct    840

tcaaatgcat ttatcgtcgc tttaaatacg gtttgaaaag agggccttct acggaaggaa    900

tgcctgagtc tatgagggaa gaatatcggc aggaacagca gaatgctgtg gatgttgacg    960

atggtcattt tgtcaacata gagctgaagt aaaaaactac cttgtttcta ctaataaccc   1020

ggcggcccaa aatgccgact cggagcgaaa gatatacctc ccccggggcc gggaggtcgc   1080

gtcaccgacc acgccgccgg cccaggcgac gcgcgacacg gacacctgtc cccaaaaacg   1140

ccaccatcgc agccacacac ggagcgcccg gggccctctg gtcaacccca ggacacacgc   1200

gggagcagcg ccgggccggg gacg                                           1224

<210> SEQ ID NO 30
```

<211> LENGTH: 1099
<212> TYPE: DNA
<213> ORGANISM: Artificial Sequence
<220> FEATURE:
<223> OTHER INFORMATION: NS

<400> SEQUENCE: 30
atggattcca acactgtgtc aagcttccag gtagactgct ttctttggca tgtccgcaaa 60
cggtttgcag accaagaact gggtgatgcc ccattcctag accggcttcg ccgggatcag 120
aagtccctga gaggaagaag cagcactctt ggtctggaca tcagaaccgc aactcgtgaa 180
ggaaaacata tagtggagcg aattttggag gaagagtcag acgaagcatt taaaatgact 240
attgcttcag tgccagctcc acgctatctc actgacatga ctcttgaaga aatgtcaaga 300
gattggttaa tgctcattcc caaacagaaa gtgacagggt ccctttgcat tagaatggac 360
caagcaatag tggacaaaaa catcacattg aaagcaaatt tcagtgtgat tttcaatcga 420
ctggaagccc taatactact tagagctttt acggatgaag gagcaatagt gggcgaaatc 480
tcaccattac cttctcttcc aggacatact gacaaggatg tcaagaatgc aattggggtc 540
ctcatcggag gatttgaatg gaatgataac acagttcgag tctctgaaac tctacagaga 600
ttcgcttgga gaagcagcaa tgaggatggg agacctccac tctctccaaa gtaggaacgg 660
gaaatggaga gaacaattaa gccagaagtt cgaagaaata agatggttga ttgaagaagt 720
acgacatagg ttaaagatta cagagaatag ctttgaacaa ataactttta tgcaagcctt 780
acaactattg cttgaagtgg agcaagagat aagaactttc tcgtttcagc ttatttaata 840
ataaaaaaca cccttgtttc tactaataac ccggcggccc aaaatgccga ctcggagcga 900
aagatatacc tcccccgggg ccgggaggtc gcgtcaccga ccacgccgcc ggcccaggcg 960
acgcgcgaca cggacacctg tccccaaaaa cgccaccatc gcagccacac acggagcgcc 1020
cggggccctc tggtcaaccc caggacacac gcgggagcag cgccgggccg gggacgccct 1080
cccggcgtca cctaatgca 1099

<210> SEQ ID NO 31
<211> LENGTH: 20
<212> TYPE: PRT
<213> ORGANISM: Artificial Sequence
<220> FEATURE:
<223> OTHER INFORMATION: H7-1

<400> SEQUENCE: 31

Gly Leu Phe Gly Ala Ile Ala Gly Phe Ile Glu Asn Gly Trp Glu Gly
1 5 10 15

Leu Ile Asp Gly
20

<210> SEQ ID NO 32
<211> LENGTH: 20
<212> TYPE: PRT
<213> ORGANISM: Artificial Sequence
<220> FEATURE:
<223> OTHER INFORMATION: H7-2

<400> SEQUENCE: 32

Glu Asn Gly Trp Glu Gly Leu Ile Asp Gly Trp Tyr Gly Phe Arg His
1 5 10 15

Gln Asn Ala Gln
20

```
<210> SEQ ID NO 33
<211> LENGTH: 20
<212> TYPE: PRT
<213> ORGANISM: Artificial Sequence
<220> FEATURE:
<223> OTHER INFORMATION: H7-3

<400> SEQUENCE: 33

Trp Tyr Gly Phe Arg His Gln Asn Ala Gln Gly Glu Gly Thr Ala Ala
1               5                   10                  15

Asp Tyr Lys Ser
            20


<210> SEQ ID NO 34
<211> LENGTH: 20
<212> TYPE: PRT
<213> ORGANISM: Artificial Sequence
<220> FEATURE:
<223> OTHER INFORMATION: H7-4

<400> SEQUENCE: 34

Gly Glu Gly Thr Ala Ala Asp Tyr Lys Ser Thr Gln Ser Ala Ile Asp
1               5                   10                  15

Gln Ile Thr Gly
            20


<210> SEQ ID NO 35
<211> LENGTH: 20
<212> TYPE: PRT
<213> ORGANISM: Artificial Sequence
<220> FEATURE:
<223> OTHER INFORMATION: H7-6

<400> SEQUENCE: 35

Lys Leu Asn Arg Leu Ile Ala Lys Thr Asn Gln Gln Phe Glu Leu Ile
1               5                   10                  15

Asp Asn Glu Phe
            20


<210> SEQ ID NO 36
<211> LENGTH: 20
<212> TYPE: PRT
<213> ORGANISM: Artificial Sequence
<220> FEATURE:
<223> OTHER INFORMATION: H7-7

<400> SEQUENCE: 36

Gln Gln Phe Glu Leu Ile Asp Asn Glu Phe Asn Glu Val Glu Lys Gln
1               5                   10                  15

Ile Gly Asn Val
            20


<210> SEQ ID NO 37
<211> LENGTH: 20
<212> TYPE: PRT
<213> ORGANISM: Artificial Sequence
<220> FEATURE:
<223> OTHER INFORMATION: H7-8

<400> SEQUENCE: 37

Asn Glu Val Glu Lys Gln Ile Gly Asn Val Ile Asn Trp Thr Arg Asp
1               5                   10                  15

Ser Ile Thr Glu
            20
```

<210> SEQ ID NO 38
<211> LENGTH: 20
<212> TYPE: PRT
<213> ORGANISM: Artificial Sequence
<220> FEATURE:
<223> OTHER INFORMATION: H7-9

<400> SEQUENCE: 38

Ile Asn Trp Thr Arg Asp Ser Ile Thr Glu Val Trp Ser Tyr Asn Ala
1               5                   10                  15

Glu Leu Leu Val
            20

<210> SEQ ID NO 39
<211> LENGTH: 20
<212> TYPE: PRT
<213> ORGANISM: Artificial Sequence
<220> FEATURE:
<223> OTHER INFORMATION: H7-10

<400> SEQUENCE: 39

Val Trp Ser Tyr Asn Ala Glu Leu Leu Val Ala Met Glu Asn Gln His
1               5                   10                  15

Thr Ile Asp Leu
            20

<210> SEQ ID NO 40
<211> LENGTH: 20
<212> TYPE: PRT
<213> ORGANISM: Artificial Sequence
<220> FEATURE:
<223> OTHER INFORMATION: H7-13

<400> SEQUENCE: 40

Arg Val Lys Arg Gln Leu Arg Glu Asn Ala Glu Glu Asp Gly Thr Gly
1               5                   10                  15

Cys Phe Glu Ile
            20

<210> SEQ ID NO 41
<211> LENGTH: 20
<212> TYPE: PRT
<213> ORGANISM: Artificial Sequence
<220> FEATURE:
<223> OTHER INFORMATION: H7-14

<400> SEQUENCE: 41

Glu Glu Asp Gly Thr Gly Cys Phe Glu Ile Phe His Lys Cys Asp Asp
1               5                   10                  15

Asp Cys Met Ala
            20

<210> SEQ ID NO 42
<211> LENGTH: 20
<212> TYPE: PRT
<213> ORGANISM: Artificial Sequence
<220> FEATURE:
<223> OTHER INFORMATION: H7-15

<400> SEQUENCE: 42

Phe His Lys Cys Asp Asp Asp Cys Met Ala Ser Ile Arg Asn Asn Thr
1               5                   10                  15

Tyr Asp His Arg
            20

-continued

```
<210> SEQ ID NO 43
<211> LENGTH: 20
<212> TYPE: PRT
<213> ORGANISM: Artificial Sequence
<220> FEATURE:
<223> OTHER INFORMATION: cHA H7/H3

<400> SEQUENCE: 43

Ala Asp Ser Glu Met Asn Lys Leu Phe Glu Lys Thr Lys Lys Gln Leu
1               5                   10                  15

Arg Glu Asn Ala
            20
```

RECOMBINANT H7N9 SUBTYPE AVIAN INFLUENZA VIRUS, INACTIVATED MARKED VACCINE AND PREPARATION METHOD THEREOF

CROSS-REFERENCE TO RELATED APPLICATIONS

This application claims priority to International Application No. PCT/CN2019/086620 filed on May 13, 2019 which claims priority to Chinese Patent Application No. 201811308245.5 entitled "RECOMBINANT H7N9 SUBTYPE AVIAN INFLUENZA VIRUS, INACTIVATED MARKED VACCINE AND PREPARATION METHOD THEREOF", filed before China's State Intellectual Property Office on Nov. 5, 2018, the entire contents of which are incorporated herein by reference.

TECHNICAL FIELD

The present invention relates to the technical field of animal vaccines, especially relates to a recombinant H7N9 subtype avian influenza virus, a marked vaccine and a preparation method thereof.

BACKGROUND

H7N9 subtype avian influenza virus is an emerging zoonotic pathogen. Since it was first reported in China in 2013, it has caused five epidemics in humans. Early H7N9 subtype avian influenza virus is low pathogenic to poultry. The poultry are asymptomatic after infection. Human infections are associated with exposure to infected poultry or contaminated live poultry markets. Up to early 2017, H7N9 subtype avian influenza virus has become a highly pathogenic virus due to the insertion of four amino acids at the HA cleavage site so that it possesses continuous basic amino acids, which has a high lethality to chicken.

For controlling the transmission of H7N9 subtype avian influenza virus in poultry and reducing the risks of human infections caused by exposure to infected poultry or contaminated environments, China has approved the use of inactivated vaccines of H7 recombinant avian influenza virus, and achieved a good prevention and control effect. However, immunized and naturally infected animals cannot be differentiated after vaccination with inactivated vaccines of recombinant avian influenza virus, causing that infected chickens cannot be confirmed serologically, and culling measures could not be taken against the infected chickens. Therefore, it is urgently needed to develop an H7 avian influenza vaccine to differentiate naturally infected from immunized animals (DIVA) to meet the technical requirements on the decontamination and fighting of H7 avian influenza.

BRIEF SUMMARY

To overcome the above disadvantages of the prior art, the present invention aims to provide a recombinant H7N9 subtype avian influenza virus, a marked vaccine and a preparation method thereof, the marked vaccine can not only accurately distinguish vaccinated from naturally infected animals, but also be used for the effective prevention and control and cleanup of the H7N9 subtype avian influenza.

For achieving the above objects, the present invention provides the following technical scheme:

The present invention provides a recombinant H7N9 subtype avian influenza virus, for which a strain JD/17 of H7N9 subtype avian influenza virus is used as parent virus and a specific peptide sequence in HA protein of the strain JD/17 is replaced with a peptide sequence in HA protein of H3 subtype;

The peptide sequence in HA protein of H3 subtype is as shown in SEQ ID No.1 of Sequence Listing;

The peptide sequence in HA protein of the strain JD/17 is as shown in SEQ ID No.2 of Sequence Listing;

The strain JD/17 of H7N9 subtype avian influenza virus has a preservation number of CCTCC No. V201862.

The present invention provides a preparation method of the recombinant H7N9 subtype avian influenza virus, comprising the following steps:

(1) To synthesize cDNA, total RNA of the strain JD/17 of H7N9 subtype avian influenza virus is extracted and subjected to reverse transcription;

(2) With the cDNA as a template, HA-1 gene segments are amplified with pair primers KS-H7-1 and JDH7H3-1-R, and HA-2 gene segments are amplified with pair primers JDH7H3-2-F and KS-H7-2;

The nucleotide sequence of KS-H7-1 is as shown in SEQ ID No.3 of Sequence Listing;

The nucleotide sequence of JDH7H3-1-R is as shown in SEQ ID No.4 of Sequence Listing;

The nucleotide sequence of JDH7H3-2-F is as shown in SEQ ID No.5 of Sequence Listing;

The nucleotide sequence of KS-H7-2 is as shown in SEQ ID No.6 of Sequence Listing; (3) To get an HA gene segment with the replaced sequence, an overlap PCR amplification with the HA-1 gene segments and HA-2 gene segments obtained in step (2) as a template is conducted; (4) The HA gene segment with the replaced sequence in step (3) is ligated to a Blunt 3 vector, and the correct sequence in the plasmid is verified by sequencing. The plasmid is digested with BsmBI and the recovered target enzyme-digested product is cloned into a pHW2000 vector. After sequence verification, the plasmid is extracted and co-transfected with expression plasmids of other 7 genes of the strain JD/17 in pHW2000 vectors, and a recombinant H7N9 subtype avian influenza virus is rescued.

Preferably, the amplification procedures for HA-1 gene segments and HA-2 gene segments are, independently:

Pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

Preferably, the amplification system for HA-1 gene segments and HA-2 gene segments is, independently: 2.5 μL 10×PCR buffer, 0.5 μL 10 mM dNTP, 0.5 μL 25 mM forward primer, 0.5 μL 25 mM backward primer, 0.5 μL high-fidelity enzyme, 2 μL DNA template and 18.5 μL ultrapure water.

Preferably, the procedures of the overlap PCR amplification are:

Pre-degeneration at 94° C. for 5 min; degeneration at 94° C. for 30 s, annealing at 54° C. for 40 s, extension at 72° C. for 1 min 40 s, 35 cycles; extension at 72° C. for 10 min.

A preparation method of a marked vaccine of the recombinant H7N9 subtype avian influenza virus provided in the present invention, comprising the following steps:

A. To get a viral allantoic fluid, the recombinant H7N9 subtype avian influenza virus or the recombinant H7N9 subtype avian influenza virus prepared with the above preparation method is inoculated into SPF chick embryonated eggs and subjected to incubation;

B. To get an inactivated viral allantoic fluid, the above viral allantoic fluid is mixed with a formaldehyde solution, the resulting mixture is inactivated with shaking at 4° C. for 24 h;

C. To get an inactivated viral allantoic fluid mixture, the above inactivated viral allantoic fluid is mixed with Tween 80 and white oil when the inactivated viral allantoic fluid has a hemagglutination titer>4 log 2;

D. To get the marked vaccine of the recombinant H7N9 subtype avian influenza virus, the above inactivated viral allantoic fluid mixture is emulsified.

Preferably, the formaldehyde solution has a volume concentration of 4%.

Preferably, the volume ratio between the viral allantoic fluid and the formaldehyde solution is 43:7.

Preferably, the volume ratio of the inactivated viral allantoic fluid, Tween 80 and white oil is 24:1:75.

The present invention provides a marked vaccine of the recombinant H7N9 subtype avian influenza virus prepared with the above preparation method.

The present invention provides a recombinant H7N9 subtype avian influenza virus, for which a strain JD/17 of H7N9 subtype avian influenza virus is used as parent virus and a peptide sequence in HA protein of the strain JD/17 is replaced with a peptide sequence in HA protein of H3 subtype; the peptide sequence in HA protein of H3 subtype is as shown in SEQ ID No.1 of Sequence Listing; the peptide sequence in HA protein of the strain JD/17 is as shown in SEQ ID No.2 of Sequence Listing; the strain JD/17 of H7N9 subtype avian influenza virus has a preservation number of CCTCC No. V201862. Based on the whole virus, the HA protein, one of the main surface glycoproteins of avian influenza virus, is modified, and the specific peptide epitope of the HA protein is replaced with the corresponding sequence in HA protein of H3 subtype to achieve the successful rescue of the virus. Meanwhile, by determining HA titers, EID50, and TCID50 of the recombinant H7N9 subtype avian influenza virus provided in the present invention, it is indicated that the rescued virus maintains similar biological characteristics of parent virus, such as high HA titers and EID50, and chickens immunized with the inactivated and emulsified recombinant H7N9 subtype avian influenza virus produce a high level of antibody, and this antibody can be distinguished from antibodies produced by chickens infected with H7N9 subtype avian influenza virus and the recombinant H7N9 subtype avian influenza virus is suitable to be the candidate strain of the marked vaccine.

Meanwhile, the recombinant H7N9 subtype avian influenza virus provided in the present invention has modification in the HA2 protein. Since the HA2 protein itself is relatively conservative, chimeric recombination is not likely to occur, and the peptide epitope in recombinant H7N9 subtype avian influenza virus is not easily mutated, the long-term and stable efficiency of the subsequently prepared new vaccine is guaranteed.

The present invention provides a marked vaccine of the recombinant H7N9 subtype avian influenza virus prepared by the above preparation method, which is obtained after inactivation on the basis of the recombinant H7N9 subtype avian influenza virus of the above solution. It is demonstrated by challenge protection test that: there are no virus shedding in the tracheal and cloaca swabs of chickens in the recombinant H7N9 subtype avian influenza virus immunization group on days 1, 3, 5 and 7 post challenge with highly pathogenic and low pathogenic H7N9 subtype viruses, the protection rate is 100%; and highly pathogenic virus or low pathogenic virus can be detected in the tracheal and cloaca swabs of chickens in parent virus immunization group (Strain JD/17) only on days 1 and 3 post challenge, the protection rate is 90%; suggesting that the immune protective effect of the inactivated marked vaccine provided in the present invention is not lower than that of the vaccine prepared with parent virus, and it has good protection rates against both highly pathogenic H7N9 subtype AIV and low pathogenic H7N9 subtype AIV.

Biological Preservation Information

H7N9 avian influenza virus(Orthomyxoviridae Alphainfluenza virus), the strain JD/17 of H7N9 subtype avian influenza virus was preserved in China Center for Type Culture Collection on Oct. 23, 2018, the address of which is Wuhan University, No. 299, Bayi Road, Wuchang District, Wuhan City, Hubei Province, China, and it is referred as CCTCC for abbreviation. The biological preservation number is CCTCC No.V201862, and the number of the virus strain is JD/17.

BRIEF DESCRIPTION OF THE DRAWINGS

FIG. 1 is the experimental process of the marked vaccine provided in an embodiment of the present invention;

DETAILED DESCRIPTION

Figure 2:
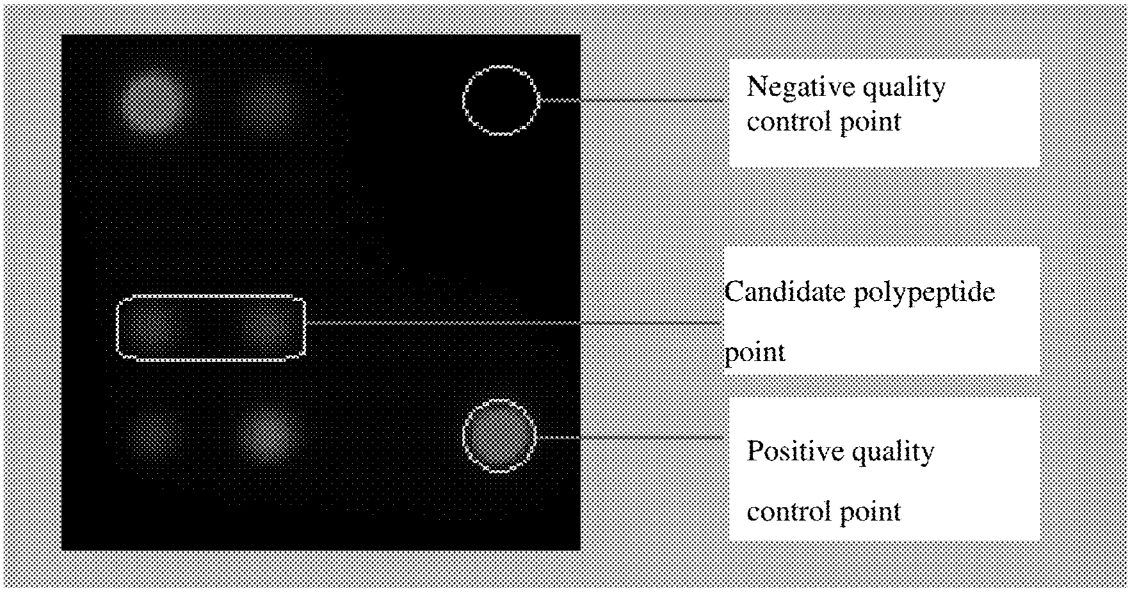
FIG. 2 is a schematic diagram showing the sampling information of protein chips.

The present invention provides a recombinant H7N9 subtype avian influenza virus, for which a strain JD/17 of H7N9 subtype avian influenza virus is used as parent virus and a specific peptide sequence in HA protein of the strain JD/17 is replaced with a peptide sequence in HA protein of H3 subtype;

The peptide sequence in HA protein of H3 subtype is as shown in SEQ ID No. 1 of Sequence Listing;

The peptide sequence in HA protein of the strain JD/17 is as shown in SEQ ID No. 2 of Sequence Listing;

The strain JD/17 of H7N9 subtype avian influenza virus has a preservation number of CCTCC No. V201862.

In the present invention, the construction of the recombinant H7N9 subtype avian influenza virus is as follow: HA2 specific epitopes of strain JD/17 are identified with a polypeptide chip method, and the HA2 epitopes are deleted or modified with a reverse genetics technique. Specifically, the HA2 specific epitope is replaced with the corresponding sequence of any subtype of influenza virus with low homology except for the H7 subtype. Due to that the peptide sequences of influenza viruses of different subtypes with low homology except for H3 subtype could not be successfully used to achieve virus rescue, so homologous peptide sequences in HA protein of H3 subtype influenza virus are selected to replace the HA2 specific epitope of strain JD/17 to develop H7N9 subtype avian influenza DIVA vaccines and its supporting detection technology, which can effectively distinguish vaccinated from naturally infected animals with serological testing methods and are used for the prevention and control and cleanup of the H7N9 subtype avian influenza.

In the present invention, the identification process of HA2 specific epitope of strain JD/17 preferably comprises the following steps:

Performing whole genome sequencing on the strain JD/17 to get the coding gene of HA protein;

Translating the nucleotide sequence of the coding gene of HA protein into a peptide sequence, intercepting the peptide sequence from 5'-end as the starting site to get the first band of polypeptide containing 20 amino acids, intercepting the peptide sequence from the $11^{th}$ amino acid of the 5'-end as the starting site to get the second band of polypeptide containing 20 amino acids, repeating as such to synthesize multiple bands of polypeptides so that there is an overlap of 10 amino acids between every two adjacent bands of polypeptides, until getting the third band of polypeptide containing 20 amino acids, the fourth band of polypeptide containing 20 amino acids, and so on, until the $N^{th}$ band of polypeptide containing 20 amino acids;

Preparing a polypeptide microarray chip with the N bands of polypeptides obtained above;

Loading the sera against different subtypes of avian influenza viruses on the polypeptide microarray chip, screening for polypeptides that bind only to antibodies against H7N9 subtype avian influenza virus according to fluorescence results, the polypeptide sequence (SEQ ID No.2) on the resulting polypeptide microarray chip is HA2 specific epitope of strain JD/17.

In the present invention, there are no specific restrictions on the types of avian influenza viruses of different subtypes, as long as adopting avian influenza virus subtypes common in the art. There are no specific restrictions on the preparation methods of serum antibodies of avian influenza virus of different subtypes, as long as adopting the preparation methods of serum antibodies well known in the art.

The present invention provides a preparation method of the recombinant H7N9 subtype avian influenza virus, comprising the following steps:

(1) To synthesize cDNA, total RNA of the strain JD/17 of H7N9 subtype avian influenza virus is extracted and subjected to reverse transcription;

(2) With the cDNA as a template, HA-1 gene segments are amplified with pair primers KS-H7-1 and JDH7H3-1-R, and HA-2 gene segments with are amplified pair primers JDH7H3-2-F and KS-H7-2;

The nucleotide sequence of KS-H7-1 is as shown in SEQ ID No.3 of Sequence Listing;

The nucleotide sequence of JDH7H3-1-R is as shown in SEQ ID No.4 of Sequence Listing;

The nucleotide sequence of JDH7H3-2-F is as shown in SEQ ID No.5 of Sequence Listing;

The nucleotide sequence of KS-H7-2 is as shown in SEQ ID No.6 of Sequence Listing;

(3) To get an HA gene segment with the replaced sequence, an overlap PCR amplification with the HA-1 gene segments and HA-2 gene segments obtained in step (2) as a template is conducted;

(4) The HA gene segment with the replaced sequence in step (3) is ligated to a Blunt 3 vector, and the correct sequence in the plasmid is verified by sequencing. The plasmid is digested with BsmBI; and the recovered target enzyme-digested product is cloned into a pHW2000 vector. After sequence verification, the plasmid is extracted and co-transfected with expression plasmids of other 7 genes of the strain JD/17 in pHW2000 vectors, and a recombinant H7N9 subtype avian influenza virus is rescued.

In the present invention, total RNA of the strain JD/17 of H7N9 subtype avian influenza virus is extracted and reverse transcribed to get a cDNA.

There are no specific restrictions on the processes of extraction and reverse transcription of the total RNA, as long as adopting the kits well known in the art.

Upon obtaining the cDNA, it is used as a template for amplifying HA-1 gene segments with pair primers KS-H7-1 and JDH7H3-1-R, and amplifying HA-2 gene segments with pair primers JDH7H3-2-F and KS-H7-2;

The nucleotide sequence of KS-H7-1 is as shown in SEQ ID No.3 of Sequence Listing;

The nucleotide sequence of JDH7H3-1-R is as shown in SEQ ID No.4 of Sequence Listing;

The nucleotide sequence of JDH7H3-2-F is as shown in SEQ ID No.5 of Sequence Listing;

The nucleotide sequence of KS-H7-2 is as shown in SEQ ID No.6 of Sequence Listing.

In the present invention, the amplification procedures for HA-1 gene segments and HA-2 gene segments are, independently and preferably:

Pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

Preferably, the amplification system for HA-1 gene segments and HA-2 gene segments is, independently: 2.5 μL 10×PCR buffer, 0.5 μL 10 mM dNTP, 0.5 μL 25 mM forward primer, 0.5 μL 25 mM backward primer, 0.5 μL high-fidelity enzyme, 2 μL DNA template and 18.5 μL ultrapure water.

Upon obtaining HA-1 gene segments and HA-2 gene segments, they are preferably checked for quality first, the procedures of which are that after the band sizes are confirmed by agarose gel electrophoresis to be correct, they are cut and recycled with a gel extraction kit (see the instructions for the steps), their concentrations and purities are determined, the test results of OD260/OD280 in the range of 1.8~2.0 would be eligible and used in the following experiments.

Upon obtaining HA-1 gene segments and HA-2 gene segments, an overlap PCR amplification is conducted with the HA-1 gene segments and HA-2 gene segments obtained in step (2) as the template, to get an HA gene segment with the replaced sequence.

In the present invention, primers used in the overlap PCR amplification are JDH7H3-1-R and JDH7H3-2-F.

In the present invention, the procedures of the overlap PCR amplification are, preferably: pre-degeneration at 94° C. for 5 min; degeneration at 94° C. for 30 s, annealing at 54° C. for 40 s, extension at 72° C. for 1 min 40 s, 35 cycles; extension at 72° C. for 10 min.

In the present invention, the system of the overlap PCR amplification is preferably 25 μL, except for DNA template of 4 μL (each 2 μL for upper and lower segments of gene), reducing the ultrapure water to 16.5 μL, with others the same as those in the above PCR amplification system.

Upon obtaining HA gene segments with the replaced sequence, the HA plasmid with the replaced sequence is co-transfected with the expression plasmids of other 7 genes of the strain JD/17, and rescued to get the recombinant H7N9 subtype avian influenza virus.

In the present invention, the HA gene segment with the replaced sequence is ligated to a Blunt 3 vector, and the correct sequence in the plasmid is verified by sequencing. The plasmid is digested with BsmBI and the recovered target enzyme-digested product is cloned into a pHW2000 vector. After sequence verification, the plasmid is extracted and co-transfected with expression plasmids of other 7 genes of the strain JD/17 in pHW2000 vectors. The other 7 genes include the following varieties: PB2, PB1, PA, NP, NA, M and NS. The detailed steps for rescue of recombinant virus by co-transfection of the extracted plasmid and expression plasmids of other 7 genes of the strain JD/17 in pHW2000 vectors can refer to the following literature: Lu Jianhong, Long Jinxue, Shao Weixing, et al. The production of attenuated H5 subtype recombinant influenza virus by reverse genetics [J]. Journal of microbiology, 2005, 45: 53-57.

In the present invention, the rescue method of virus includes the following steps: the day before transfection, 293T and MDCK cells are mixed in equal amounts and then inoculated in a 6-well cell culture plate (about $6\times10^5$ cells/well), and transfection is performed when the cell coverage reaches 80%. The transfection procedures refer to the instruction for Polyjet transfection reagents. Each transfection system contains a transcription/expression plasmid of 8 segments (300 ng/plasmid, the HA segment is the HA with the replaced sequence, the remaining are 7 segments of JD/17). 48-72 h after transfection, the transfection supernatant is harvested by 3 times repeated freezing and thawing, and is inoculated into 10-day-old SPF chick embryonated eggs at 0.3 mL/embryo. The titer of the allantoic fluid in inoculated chick embryonated eggs was determined by a hemagglutination test (HA), to verify whether the virus has been rescued successfully. Total RNA of virus is extracted from the HA positive allantoic fluid of chick embryonated eggs, and 8 segments are amplified by PCR for sequencing, if correct, the viral allantoic fluid is stored in a fridge at −70° C. ready for use.

For verifying the properties of DIVA, a H7-12 polypeptide microarray chip is used to detect the immune sera of recombinant H7N9 subtype avian influenza virus and parent virus. The results show that the immune serum of the parent virus strain JD/17 has high positive responses (6.39±0.13) against H7-12 peptide, while the immune serum of the recombinant H7N9 subtype avian influenza virus shows negative responses (0.44±0.14). It is indicated that the vaccine candidate strain has lost the epitope of H7-12, the DIVA strategy is successful.

HA titers, $EID_{50}$, and $TCID_{50}$ of the recombinant H7N9 subtype avian influenza virus are determined, the results showing that the biological characteristics of the rescued virus are similar to those of the parent virus.

A preparation method of a marked vaccine of the recombinant H7N9 subtype avian influenza virus provided in the present invention, including the following steps:

A. To get a viral allantoic fluid, the recombinant H7N9 subtype avian influenza virus or the recombinant H7N9 subtype avian influenza virus prepared with the above preparation method is inoculated into SPF chick embryonated eggs and subjected to incubation;

B. To get an inactivated viral allantoic fluid, the above viral allantoic fluid is mixed with a formaldehyde solution, the resulting mixture is inactivated with shaking at 4° C. for 24 h;

C. To get an inactivated viral allantoic fluid mixture, the above inactivated viral allantoic fluid is mixed with Tween 80 and white oil when the inactivated viral allantoic fluid has a hemagglutination titer>4 log 2;

D. To get the marked vaccine of the recombinant H7N9 subtype avian influenza virus, the above inactivated viral allantoic fluid mixture is emulsified.

In the present invention, the formaldehyde solution preferably has a volume concentration of 4%.

In the present invention, the volume ratio between the viral allantoic fluid and the formaldehyde solution is preferably 43:7.

In the present invention, the volume ratio of the inactivated viral allantoic fluid, Tween 80 and white oil is preferably 24:1:75.

The present invention provides a marked vaccine of the recombinant H7N9 subtype avian influenza virus prepared with the above preparation method It is demonstrated from a challenge protection test that: the immune protective effect of the prepared inactivated marked vaccine is not lower than that of the vaccine prepared with parent virus, and it has good protection rates against both highly pathogenic H7N9 subtype AIV and low pathogenic H7N9 subtype AIV, and its biological characteristics are not changed upon replacement.

The following embodiments present a detailed description on a recombinant H7N9 subtype avian influenza virus, a marked vaccine and a preparation method thereof provided in the present invention, however, they should not be considered to limit the protection scope of the invention.

Embodiment 1

Isolation and Identification of H7N9 Subtype Avian Influenza Virus 1.1 Virus Isolation (1) When collecting swab samples from live poultry markets, samples of trachea and cloaca of poultries are collected with sterilized swabs. Cloaca swabs should contain feces as much as possible, and trachea swabs should contain mucus as much as possible. The swabs are then broken off and stored in 2 mL eppendrof tubes containing 1 mL transporting liquid separately. The collected samples are transported in ice boxes.

(2) Treatment on clinical tissue samples: cutting up clinical tissue samples in a super clean bench and placing them in a 5 ml grinding tube with 4 mL PBS containing four antibiotics; grinding by homogenating with a homogenizer of biological samples at an uniform rate of 6500 rpm for 20 s with a pause of 10 s for 2 cycles; placing the grinding tube in a fridge at −70° C. for 10 min, then taking out to thaw, repeated freezing and thawing like this for 3 times; centrifuging the clinical samples after freezing and thawing at 8000 rpm for 10 min, then subpackaging the supernatants into eppendrof tubes, ready for use. Swabs are discarded after the samples on them are squeezed. The eppendrof tubes containing liquid are placed in a fridge at −70° C., and taken out 10 min later to thaw, repeated freezing and thawing like this for 3 times; the samples after freezing and thawing are centrifuged at 8000 rpm for 10 min, then the supernatants are subpackaged into eppendrof tubes, ready for use.

(3) Inoculation of allantoic cavity of chick embryonated egg is used for the isolation and passage of virus. The above obtained supernatants are inoculated into chick embryonated eggs. Then the chick embryonated eggs are checked every 12 h. Dead chick embryonated eggs are placed in a fridge at 4° C. for 4 h, then their allantoic fluid is harvested. After continuous check for 5 days, all the undead chick embryonated egg are placed in a fridge at 4° C. for 4 h until death. HA titers are determined as follows. The allantoic fluid is obtained aseptically from positive samples and kept at −70° C. for use. A certain amount of allantoic fluid is collected aseptically from negative samples and passaged once in SPF chick embryonated eggs to determine whether it is positive for hemagglutination. The virus in allantoic fluid is defined as the virus strain JD/17 and preserved biologically.

(4) Hemagglutination (HA) test:

① Adding 25 μL PBS into each well of a 96-well microtiter plate.

② Adding 25 μL the above allantoic fluid into the first line of wells of the 96-well microtiter plate, fold dilution from left to right until the 11th well, discarding the 25 μL coming from the 11th well, and the 12th well is used as the negative control.

③ Supplementing 25 μL PBS to each well.

④ Adding 25 μL of 1% erythrocytes to each well, the final liquid volume of each well is 75 μL, gently shaking the microtiter plate to mix the liquid in the wells, and placing the microtiter plate at room temperature (20° C.) for 40 min.

⑤ After standing for a specified period of time, tilting the V-shaped microtiter plate to make the erythrocytes in the negative control well hang like a thread; then examining other experimental wells, the dilution at which the erythrocytes do not hang like a thread completely is taken as HA titer of the virus.

1.2 Virus Indentification

Virus subtypes are identified by a hemagglutination inhibition (HI) test, the specific processes are as follows:

(1) Before the hemagglutination inhibition test, performing a hemagglutination test first to determine the HA titer of the virus to be tested at that time.

(2) Adding 25 μL PBS to each well of the 96-well microtiter plate.

(3) Separately adding 25 μL standard positive serum against H1, H3, H4, H5, H6, H7, H9, H10, H11 subtype avian influenza virus or Newcastle disease virus or Egg drop syndrome virus into the first line of wells of the 96-well microtiter plate, fold dilution from left to right until the 10th well, discarding the 25 μL coming from the 10th well, the 11th well is used as the virus positive control, and the 12th well is used as the PBS negative control.

(4) Adding 4 units of real-time formulated virus into the first 11 lines of wells of the 96-well blood coagulation plate, supplementing 25 μL PBS into the 12th line of wells, gently shaking to mix, and placing the coagulation plate at room temperature (25° C.) for 40 min, or at 4° C. for 60 min to make the serum and antigen react fully.

(5) After then, adding 25 μL of 1% chickens erythrocytes into each well, mixing well with shaking and placing at room temperature (25° C.).

(6) Tilting the microtiter plate to observe the thread hanging profile of the erythrocytes. It is indicated from thread hanging that serum and virus have reacted fully, referred as positive. The serum dilution at which complete thread hanging is read as the hemagglutination inhibition titer of the serum against the virus, that is HI titer, with the titers above 4 being marked as effective. Viruses are identified according to HI titers. There is not thread hanging in the virus positive control of the $11^{th}$ well, but there is thread hanging in the PBS negative control of the $12^{th}$ well.

1.3 Determination of 50% Egg Infectious Dose ($EID_{50}$) of Virus in Chick Embryonated Egg Viral allantoic fluid is 10-fold diluted with PBS containing four antibiotics (penicillin, streptomycin, kanamycin, and gentamycin), of which 6 dilutions ($10^{-5}$~$10^{-10}$) are chosen to inoculate 10-day-old SPF chicken embryonated eggs, with 5 chick embryonated eggs being inoculated at each dilution, 0.2 mL per egg. The inoculated chick embryonated eggs are incubated at 35° C., and checked every 12 h, until 72 h. $EID_{50}$ is finally calculated following a Reed-Muench method.

1.4 Immune Serum Preparation and Titer Determination (1) Centrifuging the strain JD/17 at 8000 r/min for 10 min, taking the supernatants to determine the HA titers of virus before inactivation.

(2) Mixing the viral allantoic fluid with an aqueous formaldehyde diluted at 1:50 at a proportion of 43:7 evenly and placing in a shaking bed at 4° C. for inactivaton for 24 h.

(3) Taking out the inactivated viral allantoic fluid to determine the hemagglutination titer after inactivation (meeting the requirements when the hemagglutination titer>4 log 2).

(4) Adding Tween 80 into the inactivated viral allantoic fluid at a proportion of 24:1, after mixing evenly, adding white oil into the inactivated virus at a proportion of 3:1 and then emulsifying to prepare the vaccine.

(5) Subcutaneously injecting 3-week-old SPF chickens at the neck with the prepared vaccines, 0.3 mL per chicken, and five SPF chickens per group.

(6) After vaccination, collecting chickens blood on days 14 and 21, isolating the serum, and determining HI titers.

1.5 Isolation and Identification Results

Through virus isolation, determining HA and HI titers, and sequencing the whole genome of the virus, one low pathogenic H7N9 subtype avian influenza virus A/Chicken/Huadong/JD/17(H7N9) (JD/17) was isolated from a poultry farm in 2017, the gene sequences of 8 segments can be seen in the supplementary materials. It is found from the determination of biological characteristics (Table 1) that this virus has high HA titers and $EID_{50}$, and chickens vaccinated with the inactivated and emulsified virus produce a high level of antibody, and this virus is suitable to be the vaccine candidate.

The test results are shown in Table 1.

TABLE 1

Determination of biological characteristics of strain JD/17

| Isolated strain | HA Titer (nlog2) | $EID_{50}$ ($Log_{10}EID_{50}$/mL) | HI Titer after immunization once (nlog2 ± SD) Day 14 | Day 21 |
|---|---|---|---|---|
| JD/17 | 10 | 9.5 | 7.3 ± 1.7 | 8.9 ± 1.1 |

Embodiment 2

Sequencing the Whole Genome

Total RNA of JD/17 viral allantoic fluid is extracted with a Trizol method, then 8 gene segments of the virus are amplified respectively with the reverse transcription PCR (RT-PCR), with the amplification primers seen in Table 2.

TABLE 2

Amplification primers for sequencing the whole genome

| Gene Segments | Primers | Primer Sequences (5'-3') | Segment Length (bp) | Sequence No. |
|---|---|---|---|---|
| PB2 | Ba-PB2-F | TATT*GGTCTC*AGGGAGCGAAAGCAGGTC | 2370 | SEQ ID No. 7 |
| | Ba -PB2-R | ATAT*GGTCTC*GTATTAGTAGAAACAAGGTC GTTT | SEQ ID No. 23 | SEQ ID No. 8 |
| PB1 | Bm-PB1-F | TATT*CGTCTC*AGGGAGCGAAAGCAGGCA | 2370 | SEQ ID No. 9 |
| | Bm-PB1-R | ATAT*CGTCTC*GTATTAGTAGAAACAAGGCA TTT | SEQ ID No. 24 | SEQ ID No. 10 |
| PA | Bm-PA-F | TATT*CGTCTC*AGGGAGCGAAAGCAGGTAC | 2263 | SEQ ID No. 11 |
| | Bm-PA-R | ATAT*CGTCTC*GTATTAGTAGAAACAAGGTA CTT | SEQ ID No. 25 | SEQ ID No. 12 |
| HA | Bm-HA-F | TATT*CGTCTC*AGGGAGCRAAAGCAGGGG | 1850 | SEQ ID No. 13 |
| | Bm-HA-R | ATAT*CGTCTC*GTATTAGTAGAAACAAGGGT GTTTT | SEQ ID No. 26 | SEQ ID No. 14 |
| NP | Bm-NP-F | TATT*CGTCTC*AGGGAGCAAAAGCAGGGTAG AT | 1602 SEQ ID No. 27 | SEQ ID No. 15 |
| | Bm-NP-R | ATAT*CGTCTC*GTATTAGTAGAAACAAGGGT ATTT | | SEQ ID No. 16 |
| NA | Ba-NA-F | TATT*GGTCTC*AGGGAGCAAAAGCAGGAGT | 1489 | SEQ ID No. 17 |
| | Ba-NA-R | ATAT*GGTCTC*GTATTAGTAGAAACAAGGAG TTTTTT | SEQ ID No. 28 | SEQ ID No. 18 |
| M | Bm-M-F | TATT*CGTCTC*AGGGAGCAAAAGCAGGTAG | 1056 | SEQ ID No. 19 |
| | Bm-M-R | ATAT*CGTCTC*GTATTAGTAGAAACAAGGTA GTTTTT | SEQ ID No. 29 | SEQ ID No. 20 |
| NS | Bm-NS-F | TATT*CGTCTC*AGGGAGCAAAAGCAGGGTGA C | 919 | SEQ ID No. 21 |
| | Bm-NS-R | ATAT*CGTCTC*GTATTAGTAGAAACAAGGGT GTTTT | SEQ ID No. 30 | SEQ ID No. 22 |

PCR amplification is conducted with primers of the above 8 gene segments. A PCR system of 25 μL is configured: 2.5 μL 10×PCR buffer, 0.5 μL dNTP (10 mM), 0.5 μL 25 mM forward primer, 0.5 μL 25 mM backward primer, 0.5 μL high-fidelity enzyme, 2 μL DNA template and 18.5 μL ultrapure water.

PCR amplification procedures: Pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

Electrophoresis is conducted on PCR products with 1% agarose, after that the target bands are recycled according to the instructions of DNA Gel Extraction Kit. DNA concentrations of the recycled PCR products are determined with a spectrophotometer. When the concentration is ≥50 ng/μL, meeting the sequencing requirements, the recycled PCR products are sent to the company together with primers for bi-directional sequencing; if the concentration of the recycled PCR products is low, the recycled products can be ligated to T3 Easy Vector and transformed to DH5a *Escherichia coli* competent cells, referring to the instruction of T3 Easy Vector for the specific method. White colonies are picked on $IPTG^+$, $X\text{-}gal^+$ and $Amp^+$ LB plates, from which plasmids are extracted with a conventional process. The plasmids are identified by EcoRI digestion. Positive plasmids are sent to the company for sequencing, to get the nucleotide sequences of the 8 gene segments.

Embodiment 3

Preparation of Chickens Immune Sera Against Different HA Subtypes of Avian Influenza Viruses Using different HA subtypes of avian influenza viruses available in the laboratory, see Table 3 for details. After inactivation and emulsification, 3-week-old SPF chickens are vaccinated (steps as above). Chickens immune sera against different HA subtypes of avian influenza viruses are prepared for screening specific epitopes of H7 subtype avian influenza virus.

TABLE 3

Information about different HA subtypes of avian influenza viruses for preparing immune sera

| No. | Virus | Subtype | Hemagglutination Titer (HA nlog2) |
|---|---|---|---|
| H1 | A/Duck/Eastern China/103/03 | H1N1 | 7 |
| H3 | A/Duck/Eastern China/852/03 | H3N2 | 6 |

TABLE 3-continued

Information about different HA subtypes of avian influenza viruses for preparing immune sera

| No. | Virus | Subtype | Hemagglutination Titer (HA nlog2) |
|---|---|---|---|
| H4 | A/Duck/Eastern China/160/02 | H4N6 | 5 |
| H5-1 | A/Mallard/Huadong/S/2005 | H5N1 | 7 |
| H5-2 | A/Chicken/Huadong/1111/16 | H5N6 | 7 |
| H5-3 | A/Chicken/Huadong/ZJ0104/16 | H5N2 | 6 |
| H6 | A/Duck/Eastern China/58/03 | H6N2 | 7 |
| H9-1 | A/Chicken/Shanghai/F/98 | H9N2 | 9 |
| H9-2 | A/Chicken/Fujian/SN/14 | H9N2 | 6 |
| H10 | A/Chicken/Huadong/RD5/13 | H10N9 | 6 |
| H11 | A/Duck/Eastern China/906/02 | H11N2 | 7 |
| H7-1 | A/Chicken/Jiangsu/JT/13 | H7N9 | 8 |
| H7-2 | A/Chicken/Jiangsu/JX05/14 | H7N9 | 8 |
| H7-3 | A/Chicken/Jiangsu/W1-8/15 | H7N9 | 7 |
| H7-4 | A/Chicken/Huadong/JD/17 | H7N9 | 10 |

Embodiment 4

Synthesis of Polypeptide and Preparation of Polypeptide Chip

Modified silicone molds (iPDMS) are purchased from SJ Biomaterisls Co., and polypeptides are synthesized by GL Biochem (Shanghai, China) Co. HA2 protein of strain JD/17 of H7N9 subtype avian influenza virus is synthesized into an overlapped polypeptide following the derived peptide sequence (10 amino acids overlapped between every two adjacent bands of polypeptides), and loaded on the modified silicone molds, synthesizing 13 bands of polypeptides totally (Table 4) (wherein, the positive quality controlling dots are goat-anti-chick IgY; and the negative quality controlling dots are sample loading buffers), which are used for preparing polypeptide chips, with the microarray sample loading information seen in Table 5 and FIG. 2.

TABLE 4

13 strips of H7 subtype HA2 polypeptides and sequences thereof

| Peptides | Sequence No. | Sequence |
|---|---|---|
| H7-1 | SEQ ID No. 31 | GLFGAIAGFIENGWEGLIDG |
| H7-2 | SEQ ID No. 32 | ENGWEGLIDGWYGFRHQNAQ |
| H7-3 | SEQ ID No. 33 | WYGFRHQNAQGEGTAADYKS |
| H7-4 | SEQ ID No. 34 | GEGTAADYKSTQSAIDQITG |
| H7-6 | SEQ ID No. 35 | KLNRLIAKTNQQFELIDNEF |
| H7-7 | SEQ ID No. 36 | QQFELIDNEFNEVEKQIGNV |
| H7-8 | SEQ ID No. 37 | NEVEKQIGNVINWTRDSITE |
| H7-9 | SEQ ID No. 38 | INWTRDSITEVWSYNAELLV |

TABLE 4-continued 13 strips of H7 subtype HA2 polypeptides and sequences thereof

| Peptides | Sequence No. | Sequence |
|---|---|---|
| H7-10 | SEQ ID No. 39 | VWSYNAELLVAMENQHTIDL |
| H7-12 | SEQ ID No. 2 | ADSEMDKLYERVKRQLRENA |
| H7-13 | SEQ ID No. 40 | RVKRQLRENAEEDGTGCFEI |
| H7-14 | SEQ ID No. 41 | EEDGTGCFEIFHKCDDDCMA |
| H7-15 | SEQ ID No. 42 | FHKCDDDCMASIRNNTYDHR |

TABLE 5

Sample loading information of protein chips

| | | | |
|---|---|---|---|
| PC | H7-1 | H7-2 | NC |
| H7-3 | H7-4 | H7-6 | H7-7 |
| H7-8 | H7-9 | H7-10 | H7-12 |
| H7-13 | H7-14 | H7-15 | PC |

Embodiment 5

Identification of Specific Epitopes of HA2 Protein of H7 Subtype Avian Influenza Virus The sera against different subtypes of avian influenza virus prepared in Experiment 2 are screened in combination with polypeptide chips, to obtain epitopes which can only bind to H7N9 subtype avian influenza virus immunized sera. The specific steps are as follows:

(1) Firstly diluting serum samples in a serum dilution buffer at a ratio of 1:100, adding 200 μL in each microarray, and incubating on a shaker for 2 h (150 r/min, 4° C.).

(2) Then flushing the microarrays with TBST (20 mM Tris-HCl, pH 6.8, 137 mM NaCl, 0.1% Tween 20) three times, adding 200 μL goat-anti-chick IgY labelled with horseradish peroxidase (HRP) diluted at a ratio of 1:25000 and incubating for 1 h, then performing the same washing steps as above.

(3) Adding 15 μL chemiluminescent substrates into the microarrays, and capturing chemiluminescent signals with a CCD camera using LAS4000 imaging system (GE, USA), to acquire the signal from each point of the microarrays.

(4) Finally saving the signals as images in a format of TIFF, then processing the chemiluminescence intensity of each peptide point and the background values at a wavelength of 635 nm with a GenePix Pro 6.0 software. The chemiluminescence intensities are converted to signal to noise ratio (SNR). SNR=(signal intensity−background intensity)/background intensity, and if SNR≥2, it is judged as positive response.

Figure 3:
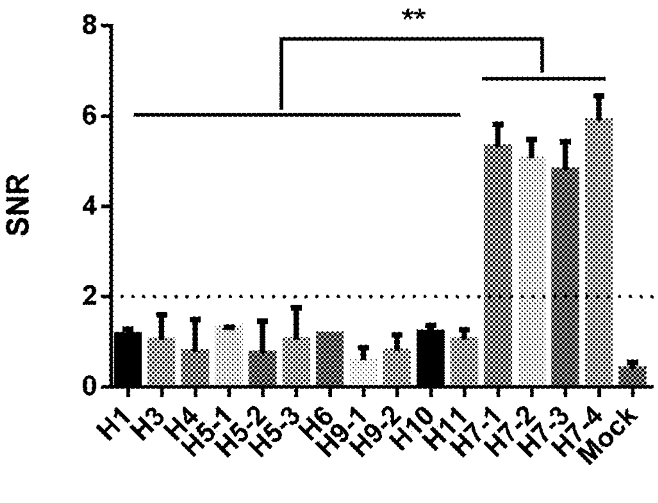
FIG. 3 is a histogram showing the response profile of various HA subtype avian influenza sera against H7-12 peptide.

FIG. 3 shows the response of each HA subtype avian influenza serum against H7-12 peptides. It is indicated from the results that only H7 subtype avian influenza sera exhibits specific positive response against H7-12 peptides (SNR>2), while other HA subtype sera exhibit negative responses against H7-12 peptides (SNR<2) (FIG. 3) (P<0.01), indicating that H7-12 peptides are epitopes which can only specifically bind to H7N9 subtype avian influenza antibody; while each HA subtype antibody shows different degree of responses against polypeptides other than H7-12 peptides (Table 6).

TABLE 6

Response profile of sera against each HA subtype avian influenza to H7-HA2 polypeptide

| Serotype | SNR (Mean ± SD) | | | | | | |
|---|---|---|---|---|---|---|---|
| | H7-1 | H7-2 | H7-3 | H7-4 | H7-6 | H7-7 | H7-8 |
| Mock | 0.08 ± 0.04 | 0.44 ± 0.27 | 0.61 ± 0.1 | 0.15 ± 0.04 | 0.11 ± 0.02 | 0.08 ± 0.05 | 0.05 ± 0.01 |
| H1 | 4.39 ± 1.5 | 1.15 ± 0.27 | 0.4 ± 0.03 | 1.48 ± 0.24 | 0.08 ± 0.02 | 0.90 ± 0.02 | 2.24 ± 0.41 |
| H3 | 1.51 ± 0.23 | 1.94 ± 0.06 | 0.85 ± 0.6 | 0.67 ± 0.35 | 1.46 ± 0.15 | 0.50 ± 0.44 | 2.58 ± 1.27 |
| H4 | 1.35 ± 0.34 | 2.38 ± 0.51 | 0.23 ± 0.02 | 1.03 ± 0.7 | 1.27 ± 0.92 | 4.42 ± 3.96 | 4.79 ± 2.39 |
| H5-1 | 0.81 ± 0.04 | 2.27 ± 0.95 | 0.83 ± 0.05 | 1.02 ± 0.54 | 1.04 ± 0.28 | 2.30 ± 0.16 | 2.32 ± 0.79 |
| H5-2 | 0.74 ± 0.22 | 3.89 ± 0.29 | 0.93 ± 0.06 | 2.37 ± 0.3 | 2.49 ± 0.24 | 0.93 ± 0.61 | 3.19 ± 0.04 |
| H5-3 | 0.45 ± 0.18 | 0.91 ± 0.65 | 0.48 ± 0.35 | 0.73 ± 0.3 | 1.52 ± 1.15 | 1.17 ± 0.29 | 3.47 ± 2.44 |
| H6 | 1.4 ± 0.39 | 3.29 ± 0.06 | 0.54 ± 0.01 | 0.89 ± 0.1 | 1.29 ± 0.16 | 0.54 ± 0.23 | 1.30 ± 0.33 |
| H9-1 | 3.78 ± 0.86 | 2.21 ± 0.62 | 3.89 ± 0.64 | 0.67 ± 0 | 0.86 ± 0.33 | 1.29 ± 0.83 | 2.98 ± 0.04 |
| H9-2 | 2.11 ± 0.45 | 1.85 ± 0.16 | 1.57 ± 0.45 | 2.12 ± 0.14 | 1.57 ± 0.09 | 1.92 ± 0.65 | 1.77 ± 0.1 |
| H10 | 3.31 ± 0.96 | 1.94 ± 0.72 | 0.42 ± 0.02 | 0.85 ± 0.31 | 1.13 ± 0.27 | 0.86 ± 0.13 | 1.50 ± 0.14 |
| H11 | 2.02 ± 0.35 | 1.08 ± 0.01 | 0.67 ± 0.37 | 1.44 ± 0.36 | 1.15 ± 0.11 | 0.76 ± 0.16 | 2.56 ± 0.97 |
| H7-1 | 7.21 ± 0.58 | 6.81 ± 0.68 | 0.10 ± 0.04 | 2.40 ± 1.92 | 0.98 ± 0.07 | 3.67 ± 2.21 | 0.73 ± 0.2 |
| H7-2 | 5.81 ± 0.19 | 1.65 ± 0.21 | 1.52 ± 0.38 | 0.83 ± 0.04 | 0.98 ± 0.68 | 1.5 ± 1.14 | 1.74 ± 0.55 |
| H7-3 | 1.64 ± 0.35 | 2.33 ± 0.12 | 7.68 ± 1.1 | 0.92 ± 0.3 | 1.13 ± 0.43 | 3.05 ± 1.87 | 2.11 ± 0.37 |
| H7-4 | 3.12 ± 0.86 | 3.93 ± 0.67 | 0.93 ± 0.06 | 0.95 ± 0.47 | 2.26 ± 0.4 | 2.55 ± 0.15 | 4.87 ± 3.44 |

| Serotype | SNR (Mean ± SD) | | | | | |
|---|---|---|---|---|---|---|
| | H7-9 | H7-10 | H7-12 | H7-13 | H7-14 | H7-15 |
| Mock | 0.61 ± 0.01 | 0.23 ± 0.08 | 0.21 ± 0.11 | 0.07 ± 0.03 | 0.16 ± 0.06 | 0.35 ± 0.08 |
| H1 | 1.31 ± 0.1 | 0.96 ± 0.39 | 1.16 ± 0.09 | 1.29 ± 0.38 | 1.63 ± 0.5 | 0.26 ± 0.08 |
| H3 | 0.87 ± 0.39 | 2.40 ± 0.3 | 1.03 ± 0.4 | 0.66 ± 0.19 | 3.09 ± 0.15 | 0.41 ± 0.14 |
| H4 | 7.00 ± 1.66 | 1.08 ± 0.68 | 0.78 ± 0.5 | 0.43 ± 0.05 | 2.34 ± 0.81 | 6.50 ± 0.98 |
| H5-1 | 3.42 ± 0.16 | 8.51 ± 1.37 | 1.31 ± 0.01 | 0.02 ± 0.02 | 3.92 ± 2.38 | 1.49 ± 0.22 |
| H5-2 | 0.73 ± 0.58 | 0.34 ± 0.11 | 0.75 ± 0.5 | 2.75 ± 0.69 | 2.13 ± 0.25 | 0.95 ± 0.2 |
| H5-3 | 0.20 ± 0.02 | 1.41 ± 0.09 | 1.05 ± 0.5 | 0.16 ± 0.03 | 2.41 ± 1.34 | 2.22 ± 1.64 |
| H6 | 4.24 ± 0.56 | 0.12 ± 0.03 | 1.17 ± 0 | 3.77 ± 1.39 | 3.43 ± 0.03 | 1.74 ± 0.64 |
| H9-1 | 0.78 ± 0.12 | 2.12 ± 0.1 | 0.59 ± 0.2 | 1.30 ± 0.28 | 8.53 ± 1 | 1.10 ± 0.24 |
| H9-2 | 1.15 ± 0.09 | 1.76 ± 0.16 | 0.8 ± 0.25 | 1.15 ± 0.1 | 6.14 ± 0.2 | 1.90 ± 0.26 |
| H10 | 1.67 ± 0.23 | 0.29 ± 0.19 | 1.21 ± 0.11 | 0.90 ± 0.2 | 9.54 ± 4.67 | 0.95 ± 0.32 |
| H11 | 1.35 ± 0.32 | 0.25 ± 0.12 | 1.05 ± 0.15 | 5.35 ± 0.52 | 3.86 ± 2.28 | 0.75 ± 0.05 |
| H7-1 | 0.82 ± 0.25 | 0.79 ± 0.27 | 5.32 ± 0.35 | 5.72 ± 0.54 | 2.47 ± 0.37 | 1.01 ± 0.06 |
| H7-2 | 0.73 ± 0.33 | 1.58 ± 0.47 | 5.06 ± 0.3 | 4.30 ± 1.06 | 3.20 ± 0.75 | 0.51 ± 0.02 |
| H7-3 | 1.79 ± 0.58 | 2.41 ± 0.24 | 4.8 ± 0.45 | 2.92 ± 1.19 | 4.17 ± 0.08 | 1.31 ± 0.56 |
| H7-4 | 2.47 ± 0 | 1.36 ± 0.3 | 5.90 ± 0.39 | 4.85 ± 2.12 | 3.11 ± 0.74 | 1.09 ± 0.01 |

Embodiment 6

Preparation of H7-12 Peptide Immune Serum and Verification of Epitopes

1. Preparation of H7-12 Peptide Immune Serum

The screened H7-12 peptides are conjugated with BSA to get a H7-12-BSA conjugate. The conjugate is used to prepare immunological antigens, which are used in the immunization of SPF chickens to prepare polyclonal antisera. The immunization procedures are as follows:

(1) Primary immunization: taking 50 μg polypeptide-BSA conjugate (dissolved in 250 μL PBS), into which is added an equal amount of Freund's complete adjuvant, emulsifying repeatedly, until the emulsion phas is no longer stratified. Chickens are injected subcutaneously at multi-points of the neck for immunization.

(2) Secondary immunization at 3 weeks after the primary immunization: taking the same dose of polypeptide-BSA conjugate, into which is added an equal amount of Freund's uncomplete adjuvant, emulsifying repeatedly. Chickens are injected subcutaneously at multi-points of the neck for immunization.

(3) Harvesting sera from immunized chicken 3 weeks later.

2. Indirect Immunofluorescence Assay (1) Culturing CEF cells in a 96-well plate, when the cells have grown to 80%, discarding the culture medium, and washing with PBS for 3 times.

(2) Diluting each HA subtype of AIV (H1, H3, H4, H5, H6, H7, H9, H10) with DMEM without antibiotics and serum, adding the diluted virus into wells, 100 μL per well.

(3) At the same time, using normal uninoculated CEF cells as the blank control.

(4) After culturing for 12 h, discarding the culture medium, washing with PBST for 3 times, 5 min for each time, then fixing with pre-cold methanol at 4° C. for 15 min; washing with PBST for 3 times, 5 min for each time, and patting dry on absorbing papers.

(5) Diluting the chicken sera at a ratio of 1:1000, adding into a 96-well plate, 200 μL/well, and reacting at 37° C. for 1.5 h. And adding H7 monoclonal antibody and negative serum, which are used as the positive control and the negative control, respectively.

(6) Washing with PBST for 3 times, 5 min for each time, adding goat-anti-chick FITC-IgG diluted at 1:500 in dark, 50 μL/well, and reacting for 1 h.

(7) Washing with PBST for 3 times, 5 min for each time, observing under a fluorescence microscope, the appearance of specific bright green fluorescence well shows positive, otherwise it is negative.

Figure 4:
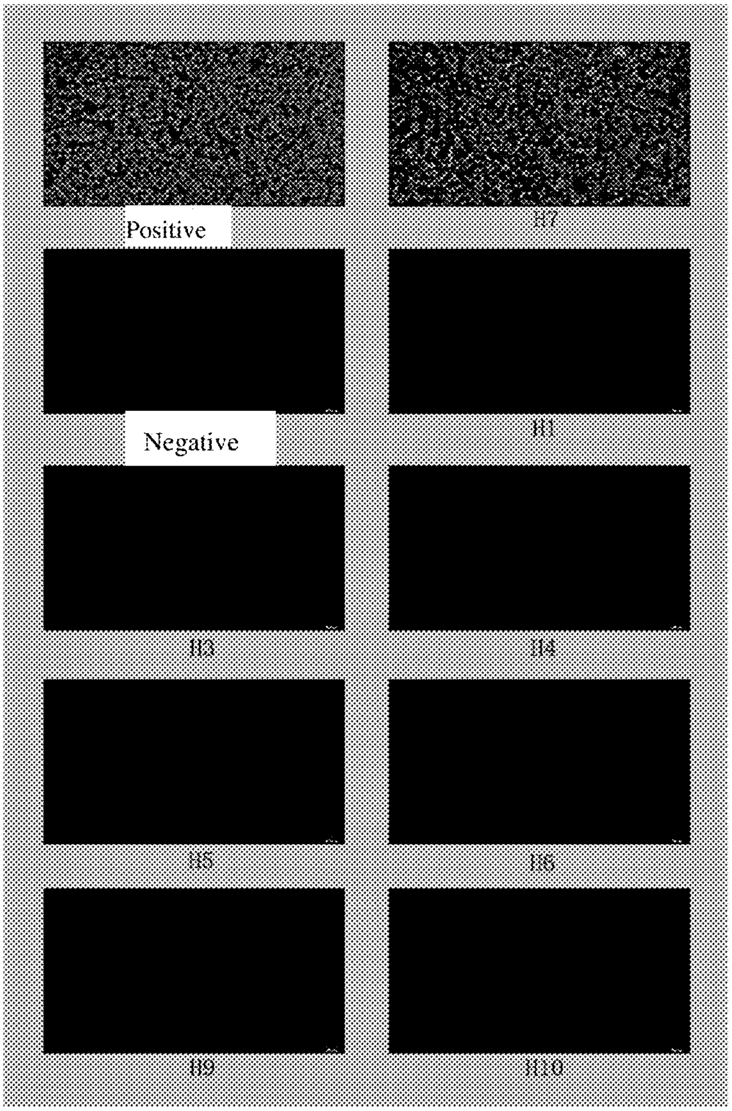
FIG. 4 shows the specificities of sera from chicken immunized with polypeptide-conjugate verified by an indirect immunofluorescence assay.

Results: it shows that for the chicken sera prepared with the polypeptide-conjugate, the specific fluorescence is observed only against H7 subtype avian influenza, and there is no specific fluorescence observed against other subtypes of virus samples, indicating that this polypeptide epitope is a specific epitope of H7 subtype avian influenza virus, with the results seen in FIG. 4.

Embodiment 7

Figure 5:
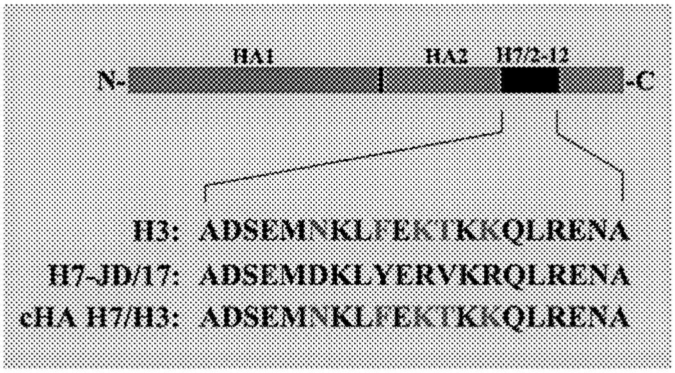
FIG. 5 is a construction plan for sequence substitution of the vaccine strain, showing the replacement of HA2-12 peptides in HA, with the amino acid ADSEMDKLYERVKRQLRENA (SEQ ID NO:2) in the H7-12 peptide region of strain JD/17 being replaced by a sequence in the HA protein of the HT subtype (ADSEMNKLFEKTKKQLRENA) (SEQ ID NO:43) via an Overlap-PCR technique.

Construction of H7N9 Subtype Recombinant Avian Influenza Virus Modified with HA2 Protein Epitope Replacement of Epitope With the screened vaccine candidate strain JD/17 as the backbone, HA2-12 peptides in HA are replaced by replacing an amino acid (ADSEMDKLYERVKRQLRENA) (SEQ ID NO:2) in H7-12 peptide region of strain JD/17 with a sequence in HA protein of H3 subtype (ADSEMNKLFEKTKKQLRENA) (SEQ ID NO:43) by an Overlap-PCR technique (primers seen in Table 7), as shown in FIG. 5.

TABLE 7

Overlap PCR primers

| Gene | Name of primers | SequenceNo. | Sequence of primers |
|---|---|---|---|
| HA-1 | KS-H7-1 | SEQ ID No. 3 | GACCTCCGAAGTTGGGGGGGAGCAAAAGCAGGGGATACAAAATGA |
| | JDH7H3-1-R | SEQ ID No. 4 | AAAAATTTCGTTCAGTTTCAACATTTCTGAATCAGCCAGA |
| HA-2 | JDH7H3-2-F | SEQ ID No. 5 | TGAACGAAATTTTTAAAATGCAGCTGAGAGAGAATGCTGA |
| | KS-H7-2 | SEQ ID No. 6 | GCATTTTGGGCCGCCGGGTTATTAGTAGAAACAAGGGTGTTTTTTCCA |

With cDNA of JD/17 as the template, the target segments are amplified with PCR. A 25 μL system is configured: 2.5 μL 10×PCR buffer, 0.5 μL dNTP (10 mM), 0.5 μL 25 mM forward primer, 0.5 μL 25 mM backward primer, 0.5 μL high-fidelity enzyme, 2 μL DNA template and 18.5 μL ultrapure water.

The procedures of PCR amplification are as follows: pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

PCR products, HA-1 and HA-2, are identified by agarose gel electrophoresis. If the bands are identified to be correct, they are cut and recycled with a gel extraction kit (see the instructions for the steps). Concentrations and purities are determined (OD260/OD280 is in the range of 1.8~2.0). Then Overlap-PCR is conducted with the gel extraction products of the upper and lower segments of HA gene as the template. The system is still 25 μL, except that the DNA template is 4 μL (2 μL for the upper and lower segments of the gene), the ultrapure water is reduced to 16.5 μL, other components are the same as in the above PCR system; for the amplification procedures, the time for extension at 72° C. is changed to 1 min 40 s, others are the same as in the above PCR amplification procedures.

The HA gene segment with the replaced sequence is ligated to a Blunt 3 vector, and the correct sequence in the plasmid is verified by sequencing. The plasmid is digested with BsmBI and the recovered target enzyme-digested product is cloned into a pHW2000 vector. After sequence verification, the plasmid is extracted and co-transfected with expression plasmids of other 7 genes of the strain JD/17 in pHW2000 vectors. The other 7 genes include the following varieties: PB2, PB1, PA, NP, NA, M and NS.

Rescue method of virus: the day before transfection, 293T and MDCK cells are mixed in equal amounts and then inoculated in a 6-well cell culture plate (about $6\times10^5$ cells/well), and transfection is performed when the cell coverage reaches 80%. The transfection procedures refer to the instruction for Polyjet transfection reagents. Each transfection system contains a transcription/expression plasmid of 8 segments (300 ng/plasmid, the HA segment is the HA gene segment with the replaced sequence, the remaining are 7 segments of JD/17). 48-72 h after transfection, freezing and thawing are repeated for 3 times, the transfection supernatant is harvested, and 10-day-old SPF chick embryonated eggs are inoculated at 0.3 mL/eggs. The titer of inoculated chick embryonated eggs was determined by a hemagglutination test (HA), to verify whether the virus has been rescued successfully. Total RNA of virus is extracted from the allantoic fluid of positive chick embryonated eggs, and 8 segments are amplified by PCR for sequencing, if correct, the viral allantoic fluid is stored in a fridge at −70° C. ready for use.

Embodiment 8

Rescue of the Recombinant DIVA Vaccine Candidate Strain with a Reverse Genetics Approach (1) Firstly growing 293T and MDCK cells in a 35 mm culture dish to abundance of 70~80%.

(2) Transfection following Polyfect guideline, pipetting and discarding the transfection liquid 6 h later, and adding cell maintenance medium (DMEM culture medium containing 1% fetal calf serum and 2 μg/mL TPCK-trypsin) into the culture dish.

(3) Forty-eight hours after the transfection, taking out the transfection culture dish, freezing and thawing for 3 times, and blowing uniformly, taking the supernatant to inoculate 10-day-old SPF chick embryonated eggs, 0.3 mL/egg.

(4) Seventy-two hours after the inoculation, harvesting the allantoic liquid and determining virus titers by a hemagglutination test (HA); if it is preliminarily judged as successful rescue by the titers, it is named as cHA H7/H3.

(5) After passaging the recombinant vaccine candidate over chick embryonated eggs for 5 generations, sequencing the virus genome to verify the genetic stability of the recombinant virus.

(6) 50% tissue culture infectious dose, $TCID_{50}$.

The day before inoculation, CEF cells are inoculated into a 96-well cell culture plate. When the cells form a monolayer, the culture supernatants are pipetted and discarded, and washed with sterile PBS for 3 times. Subsequently, a viral allantoic fluid which is continuously 10-fold diluted is inoculated to the cell surfaces, in which the dilution for inoculation is $10^{-4}$~$10^{-9}$, with 4 wells inoculated for each dilution at 0.1 mL/well. The infected cells are continually cultured at 37° C. and 5% $CO_2$. 72 h later, the number of positive infected wells are counted with a hemagglutination test, and a Reed-Muench method is used to calculate $TCID_{50}$.

Embodiment 9

Determination of Biological Characteristics of DIVA Vaccine Candidate Strain cHA H7/H3

HA titers, $EID_{50}$, and $TCID_{50}$ of cHA H7/H3 are determined. The results show that the rescued vaccine candidate strain cHA H7/H3 has similar biological characteristics to that of its parent virus, the biological characteristics are not changed by replacement of target epitope (Table 8).

TABLE 8

Determination of biological characteristics of vaccine candidate strain and its parent virus

| Virus Strain | Virus Titer | | |
|---|---|---|---|
| | $EID_{50}$($Log_{10}EID_{50}$/mL) | $TCID_{50}$($Log_{10}TCID_{50}$/mL) | HA titer ($Log_2$HAT) |
| JD/17 | 9.33 | 6.0 | 10 |
| cHA H7/H3 | 9.67 | 6.0 | 10 |

Embodiment 10

Verification on the DIVA Properties of the Recombinant Vaccine Candidate Strain

1. Experimental Design (1) Preparing sera from SPF chicken immunized with the obtained recombinant virus, simultaneously using wild-type virus strain JD/17 as the control, the preparation steps of sera are the same as above.

(2) On day 21 after primary immunization, harvesting sera from the immunized chicken.

(3) Determining the prepared sera with the polypeptide chip prepared with H7-12 peptides, the steps are the same as above.

2. Experimental Results

Figure 6:
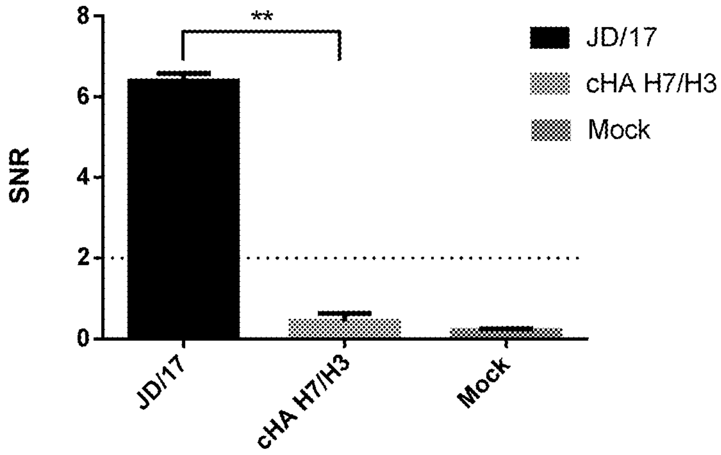
FIG. 6 is a histogram showing the response profile of sera from chickens immunized with vaccine candidate strains and parent virus against H7-12 peptide.

The results show that, the immune serum of wild-type virus strain JD/17 has high positive responses (6.39±0.13) against H7-12 peptides, while the immune sera of vaccine candidate strain all exhibit negative responses (0.44±0.14), see FIG. 6. It is indicated that this vaccine candidate strain has lost the epitope of H7-12, the DIVA strategy is successful.

Embodiment 11

Preparation of Inactivated Marked Vaccine (1) Centrifuging the vaccine candidate strain cHA H7/H3 at 8000 r/min for 10 min, then taking the supernatant to determine HA titers before inactivation of the virus.

(2) Mixing the viral allantoic fluid and a formaldehyde solution with a volume concentration of 4% at a proportion of 43:7 evenly and placing in a shaking bed at 4° C. for inactivation for 24 h.

(3) Taking out the inactivated viral allantoic fluid to determine the hemagglutination titer after inactivation (meeting the requirements when the hemagglutination titer>4 log 2)

(4) Adding Tween 80 into the inactivated viral allantoic fluid at a proportion of 24:1, after mixing evenly, adding white oil into the inactivated virus at a proportion of 3:1 and then emulsifying to prepare the vaccine.

Embodiment 12

Challenge Protection Test

1. Experimental Design and Immunoprotection Assay (1) Randomly dividing 21-day-old SPF chickens into 7 groups, with 10 for each group, wherein there are 4 immunized groups, 2 challenge control groups and 1 healthy control group.

(2) Emulsifying the parent virus strain JD/17 and the vaccine candidate strain cHA H7/H3 at the same $EID_{50}$ dose, with steps the same as above.

(3) Subcutaneously injecting an oil emulsion inactivated vaccine at the neck, 0.3 mL per chick.

(4) After vaccination, harvesting sera from chicken on days 14 and 21, and determining HI titers.

(5) On day 21 after vaccination, challenging the immunized groups and the challenge control groups with $10^6$ $EID_{50}$ low pathogenic virus strain JD/17 (H7N9) and high pathogenic virus strain XT/17 (H7N9) virus by ways of intranasal and eye droppings.

(6) After the challenge, observing and recording the morbidity and mortality profiles of each group of chickens every day, continuously check for 14 days, and calculating the survival rate of each group.

(7) On days 1, 3, 5 and 7 post challenge, collecting cloaca and tracheal swabs from all the test chickens.

(8) Through treatment, inoculating the swab samples into two 10-day-old SPF chick embryonated eggs, then determining the virus shedding profile of each group of chickens.

2. Test Results

HI test results show that (Table 9), on day 21 after the primary immunization, HI titers against the low pathogenic H7N9 subtype virus strain JD/17 can reach 8.8±0.4~9.2±0.6; and HI titers against the highly pathogenic H7N9 subtype virus strain XT/17 can reach 4.5±1.3~5.2±0.7. Challenge was conducted 21 days after immunization. On the second day of challenge, mental depression began to appear in the control group challenged with the highly pathogenic virus strain XT/17, and part of them died; on day 3 after the challenge, all of them died. However, for the control group challenged with the low pathogenic virus and the 4 immunized groups, there was no phenomenon of morbidity, and they were all in a good state of mind.

The virus shedding profile after challenge of all groups of test chickens was determined (Table 9), for the control group challenged with the low pathogenic virus, the virus shedding started on the first day, and peaked on the third and fifth day; for the control group challenged with the highly pathogenic virus, the virus shedding also started on the first day, and all died on the third day. For the cHA H7/H3 immunized group, on days 1, 3, 5 and 7 after challenge with both low pathogenic and highly pathogenic H7N9 subtype virus, there was no virus detected in tracheal or cloaca swabs, the protection rate was 100%; while virus shedding against highly pathogenic or low pathogenic AIV was only detected on days 1 and 3 for groups immunized with the parent virus.

TABLE 9

Virus shedding and survival profiles of each group of chickens after immunization and challenge

| Groups | HI titers | challenge virus strain | Virus shedding Rate (%) 1 d Tracheal | 1 d Cloaca | 3 d Tracheal | 3 d Cloaca | 5 d Tracheal | 5 d Cloaca | 7 d Tracheal | 7 d Cloaca | Protection Rate (%) |
|---|---|---|---|---|---|---|---|---|---|---|---|
| JD/17 | 8.8 ± 0.4[a] (5.1 ± 0.8)[b] | JD/17 | 0/10 | 0/10 | 1/10 | 0/10 | 0/10 | 0/10 | 0/10 | 0/10 | 90 |
| | 9.1 ± 0.5 (5.2 ± 0.7) | XT/17 | 1/10 | 0/10 | 0/10 | 0/10 | 0/10 | 0/10 | 0/10 | 0/10 | 90 |
| cHA H7/H3 | 9.0 ± 0.8 (4.5 ± 1.3) | JD/17 | 0/10 | 0/10 | 0/10 | 0/10 | 0/10 | 0/10 | 0/10 | 0/10 | 100 |
| | 9.2 ± 0.6 (5.0 ± 0.6) | XT/17 | 0/10 | 0/10 | 0/10 | 0/10 | 0/10 | 0/10 | 0/10 | 0/10 | 100 |
| Challege | 0 | JD/17 | 8/10 | 1/10 | 10/10 | 6/10 | 9/10 | 6/10 | 3/10 | 0/10 | — |
| Control | 0 | XT/17 | 6/10 | 1/10 | 3/3 | 3/3 | NS[c] | NS | NS | NS | — |

[a]HI against parent virus;

[b]HI titers against strain XT/17;

[c]no survival.

It is indicated from above that, the immune protection effect of the inactivated vaccine prepared with the vaccine candidate strain cHA H7/H3 is not lower than that of the vaccine prepared with the parent virus, and it has very good protection rates against both highly pathogenic H7N9 subtype AIV and low pathogenic H7N9 subtype AIV.

Embodiment 13

Detection on Sera of Naturally Infected Chickens with a Polypeptide Chip

1. Experimental Design (1) Preparing five 3-week-old SPF chickens with foot markers, and simultaneously taking three SPF chickens as the control group.

(2) Determining $EID_{50}$ of the parent virus strain JD/17, and challenge the five SPF chickens at a dose of $10^6$ $EID_{50}$ by ways of intranasal and eye droppings.

(3) On days 3, 5, 7, 14, 21 and 28 post challenge, harvesting sera from these five SPF chickens and the control group respectively, and storing at −20° C. ready for use.

(4) Performing a hemagglutination inhibition test (HI) on sera of naturally infected chickens, and determining the HI titers.

(5) Detecting the sera of naturally infected chickens with a polypeptide chip prepared with H7-12 peptides, and calculating SNR values.

2. Test Results

The HI test results show that, HI titers were successfully detected on day 7 post virus infection (4.6±0.5); the results on the polypeptide chip show that, the SNR value determined on day 3 of virus infection indicated the appearance of a positive response (SNR=2.33±0.15). As the time of infection increased, the SNR value became higher, with the specific results shown in Table 10.

TABLE 10

Detection of SPF chicken sera at different stages of infection by the HI test and a polypeptide chip

| Days post infection | Mark number of infected serum HI (log2) ± SD | SNR (Mean ± SD) |
|---|---|---|
| 0 | 0 | 0.16 ± 0.07 |
| 3 dpi | 0 | 2.33 ± 0.15 |
| 5 dpi | 0 | 2.49 ± 0.19 |
| 7 dpi | 4.6 ± 0.5 | 3.53 ± 0.27 |
| 14 dpi | 6.4 ± 0.5 | 4.63 ± 0.18 |
| 21 dpi | 7.0 ± 0.6 | 4.69 ± 0.12 |
| 28 dpi | 7.6 ± 1.4 | 4.69 ± 0.11 |

The description of the above embodiments is only intended to assist in the understanding the method and core concept of the invention. It should be noted that for persons with ordinary skills in the art, several improvements and modifications can be made to the invention without deviating from the principle of the invention, which also fall within the protection scope of the claims of the invention. Multiple changes to these embodiments are obvious to professionals in the art, and the general principles defined herein may be realized in other embodiments without deviating from the spirit or scope of the invention. Therefore, the invention shall not be limited to such embodiments as described herein, but shall conform to the widest scope consistent with the principles and novel features disclosed herein.

What is claimed is:

1. A method for preparing a recombinant H7N9 subtype avian influenza virus, the method comprising the steps of:

(1) extracting the total RNA of the H7N9 subtype avian influenza JD/17 strain, and reverse transcribing the total RNA to obtain the cDNA of the H7N9 subtype avian influenza JD/17;

(2) obtaining HA-1 and an HA-2 gene fragments via amplifying at least a portion of the HA-1 gene of the cDNA of the H7N9 subtype avian influenza JD/17 with the primer pair KS-H7-1 and JDH7H3-1-R, and at least a portion of the HA-2 gene of the cDNA of the H7N9 subtype avian influenza JD/17 with the primer pair JDH7H3-2-F and KS-H7-2;

wherein the nucleotide sequence of the KS-H7-1 primer is the nucleotide sequence of SEQ ID No. 3;

wherein the nucleotide sequence of the JDH7H3-1-R primer is the nucleotide sequence of SEQ ID No. 4;

wherein the nucleotide sequence of the JDH7H3-2-F primer is the nucleotide sequence of SEQ ID No. 5;

wherein the nucleotide sequence of the KS-H7-2 primer is the nucleotide sequence of SEQ ID No. 6;

(3) using the HA-1 and HA-2 gene fragments obtained in step (2) as templates, performing overlapping PCR amplification to obtain sequence-replaced HA gene fragments; and (4) obtaining a recombinant H7N9 subtype avian influenza virus strain via ligating the sequence-replaced HA gene fragment obtained in step 3 to a Blunt3 vector to obtain an intermediate transition plasmid, digesting the intermediate transition plasmid with a BsmBI enzyme to obtain a digested target product, cloning the digested target product into a pHW2000 vector to obtain a HA gene transfection vector plasmid, and transfecting the HA gene transfection vector plasmid with an expression plasmid constructed from the other 7 genes of the JD/17 strain in pHW2000 vectors.

2. The method of claim 1, wherein the amplification procedures for the HA-1 gene segments and the HA-2 gene segments comprise the steps of: pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

3. The method of claim 1, wherein the amplification system for the HA-1 gene segments and the HA-2 gene segments comprises: 2.5 μL 10×PCR buffer, 0.5 μL 10 mM dNTP, 0.5 μL 25 mM forward primer, 0.5 μL 25 mM backward primer, 0.5 μL high-fidelity enzyme, 2 μL DNA template and 18.5 μL ultrapure water.

4. The method of claim 1, wherein the overlap PCR amplification procedure comprises the steps of: pre-degeneration at 94° C. for 5 min; degeneration at 94° C. for 30 s, annealing at 54° C. for 40 s, extension at 72° C. for 1 min 40 s, 35 cycles; extension at 72° C. for 10 min.

5. A recombinant H7N9 subtype avian influenza virus of claim 1, characterized in that the H7N9 subtype avian influenza virus JD/17 strain is used as a parental virus strain, and further characterized in that at least a portion of the HA gene that encodes for the peptide sequence of the HA protein of the JD/17 strain is replaced with at least a portion of the HA gene that encodes for a peptide sequence of the HA protein of an H3 subtype influenza virus;

wherein at least a portion of the nucleotide sequence of the HA gene of the recombinant H7N9 subtype avian influenza virus encodes the peptide sequence of SEQ ID No. 1;

wherein at least a portion of the nucleotide sequence of the HA gene of the parental virus strain encodes the peptide sequence of SEQ ID No. 2; and wherein the parental virus strain comprises the JD/17 strain of H7N9 subtype avian influenza virus having the biological preservation number CCTCC No. V201862.

6. A method of a preparing a marked vaccine for the recombinant H7N9 subtype avian influenza virus of claim 5, the method comprising the steps of:

A. obtaining a viral allantoic fluid via inoculating the recombinant H7N9 subtype avian influenza virus of claim 5 into SPF chicken embryos and incubating the inoculated SPF chicken embryos;

B. obtaining an inactivating viral allantoic fluid via mixing the viral allantoic fluid obtained in step A with a formaldehyde solution, and inactivating the resulting mixture via shaking at 4° C. for 24 h;

C. when the inactivated viral allantoic fluid has a hemagglutination titer greater than 4 log 2, obtaining an inactivating viral allantoic fluid mixture via sequentially mixing the inactivated viral allantoic fluid obtained in step B with Tween 80 and white oil;

D. obtaining a marked vaccine for the recombinant H7N9 subtype avian influenza virus via emulsifying the inactivated viral allantoic fluid mixture obtained in step C.

7. The method of claim 6, wherein the recombinant H7N9 subtype avian influenza virus is prepared via the steps of:

(1) extracting the total RNA of the H7N9 subtype avian influenza JD/17 strain, and reverse transcribing the total RNA to obtain the cDNA of the H7N9 subtype avian influenza JD/17;

(2) obtaining HA-1 and an HA-2 gene fragments via amplifying at least a portion of the HA-1 gene of the cDNA of the H7N9 subtype avian influenza JD/17 with the primer pair KS-H7-1 and JDH7H3-1-R, and at least a portion of the HA-2 gene of the cDNA of the H7N9 subtype avian influenza JD/17 with the primer pair JDH7H3-2-F and KS-H7-2;
wherein the nucleotide sequence of the KS-H7-1 primer is the nucleotide sequence of SEQ ID No. 3;
wherein the nucleotide sequence of the JDH7H3-1-R primer is the nucleotide sequence of SEQ ID No. 4;
wherein the nucleotide sequence of the JDH7H3-2-F primer is the nucleotide sequence of SEQ ID No. 5;
wherein the nucleotide sequence of the KS-H7-2 primer is the nucleotide sequence of SEQ ID No. 6;
(3) using the HA-1 and HA-2 gene fragments obtained in step 2 as templates, performing overlapping PCR amplification to obtain sequence-replaced HA gene fragments; and
(4) obtaining a recombinant H7N9 subtype avian influenza virus strain via ligating the sequence-replaced HA gene fragment obtained in step (3) to a Blunt3 vector to obtain an intermediate transition plasmid, digesting the intermediate transition plasmid with a B smBI enzyme to obtain a digested target product, cloning the digested target product into a pHW2000 vector to obtain a HA gene transfection vector plasmid, and transfecting the HA gene transfection vector plasmid with an expression plasmid constructed from the other 7 genes of the JD/17 strain in pHW2000 vectors.

8. The method of claim 7, wherein the amplification procedures for the HA-1 gene segments and the HA-2 gene segments comprise the steps of: pre-degeneration at 94° C. for 5 min; degeneration at 94° C. for 30 s, annealing at 54° C. for 40 s, extension at 72° C. for 1 min 30 s, 35 cycles; extension at 72° C. for 10 min.

9. The method of claim 7, wherein the amplification system for the HA-1 gene segments and the HA-2 gene segments comprises: 2.5 μL 10×PCR buffer, 0.5 μL 10 mM dNTP, 0.5 μL 25 mM forward primer, 0.5 μL 25 mM backward primer, 0.5 μL high-fidelity enzyme, 2 μL DNA template and 18.5 μL ultrapure water.

10. The method of claim 7, wherein the overlap PCR amplification procedure comprises the steps of: pre-degeneration at 94° C. for 5 min; degeneration at 94° C. for 30 s, annealing at 54° C. for 40 s, extension at 72° C. for 1 min 40 s, 35 cycles; extension at 72° C. for 10 min.

11. The method of claim 6, wherein the formaldehyde solution has a concentration of 4% by volume.

12. The method of claim 6, wherein the volume ratio of the viral allantoic fluid to the formaldehyde solution is 43:7.

13. The method of claim 6, wherein the volume ratio of the inactivated viral allantoic fluid to the Tween 80 and to the white oil is 24:1:75.

14. A marked vaccine for a recombinant H7N9 subtype avian influenza virus, the marked vaccine being prepared according to the method of claim 6.

* * * * *